United States Patent [19]
Cole

[11] Patent Number: 5,296,910
[45] Date of Patent: Mar. 22, 1994

[54] METHOD AND APPARATUS FOR PARTICLE ANALYSIS

[75] Inventor: Reagan Cole, Little Rock, Ark.

[73] Assignee: University of Akransas, Little Rock, Ark.

[21] Appl. No.: 956,296

[22] Filed: Oct. 5, 1992

[51] Int. Cl.$^5$ .................. G01P 3/36; G01N 15/02; G01N 21/00
[52] U.S. Cl. .................. 356/28.5; 356/336; 356/342
[58] Field of Search .................. 356/28.5, 336, 342

[56] References Cited

U.S. PATENT DOCUMENTS

| | | | |
|---|---|---|---|
| 3,743,420 | 7/1973 | Iten et al. | 356/28 |
| 4,284,351 | 8/1981 | Alldritt et al. | 356/28.5 |
| 4,633,714 | 1/1987 | Mazumder et al. | |
| 4,829,838 | 5/1989 | Clift et al. | |
| 4,830,494 | 5/1989 | Ishikawa et al. | |
| 4,854,705 | 8/1989 | Bachalo | 356/336 |
| 4,986,659 | 1/1991 | Bachalo | 356/336 |

OTHER PUBLICATIONS

"Aerodynamic Particle Size Measurement by Laser-Doppler Velocimetry", Particle Technology Laboratory Pub. No. 392, J. Aerosol Sci. Vol. 11 pp. 139-150.
"The Amplitude of Vibration of Aerosol Droplets in a Sonic Field", Contr. No. 701 from the Chemical Laboratory of Indiana, University, Jul. 1956, pp. 989-996.
"Aerosol size spectrum analysis using relaxation time measurement", App. Physics Letters, vol. 26, No. 4, 15 Feb. 1975, pp. 193-195.
Wilson et al, J. Aeroso. Sci., vol. 11, pp. 139-150, Pergamon Press Ltd, 2 Jul. 1979.
Gucker et al; Chemical Laboratory of Indiana Univ., Bloomington, Ind.; p. 989; 5 Mar. 1956.
Kirsch et al, App. Physics Let., vol. 26, #4, 15 Feb. 1975; p. 193.

*Primary Examiner*—Stephen C. Buczinski
*Attorney, Agent, or Firm*—Hermann, Ivester, Hill, Steadman & Simpson

[57] ABSTRACT

An aerosol spectrometer combines the features of forced motion instruments and optical particle sizers. The motion of suspended particles in multiple force fields is used to obtain density, diameter, electrical charge, magnetic moment and other physical attributes of individual particles. Measurements are possible without the need for precision size standards. Optical scattering parameters are also extracted, namely scattering magnitude and visibility. This allows calibration of the optical sizer based on independently measured size parameters also without the need for precision standards. Since the optical counter is extremely rapid, it is possible to apply feedback control to the application of force on the particles and to the sample dispensing apparatus as well. Because of the large amount of information extracted from single particle events, and because of the speed with which the measurements are made it is possible to characterize the distribution of particle attributes in an ensemble of particles such as a naturally occurring aerosol or a dispersed powder sample.

29 Claims, 18 Drawing Sheets

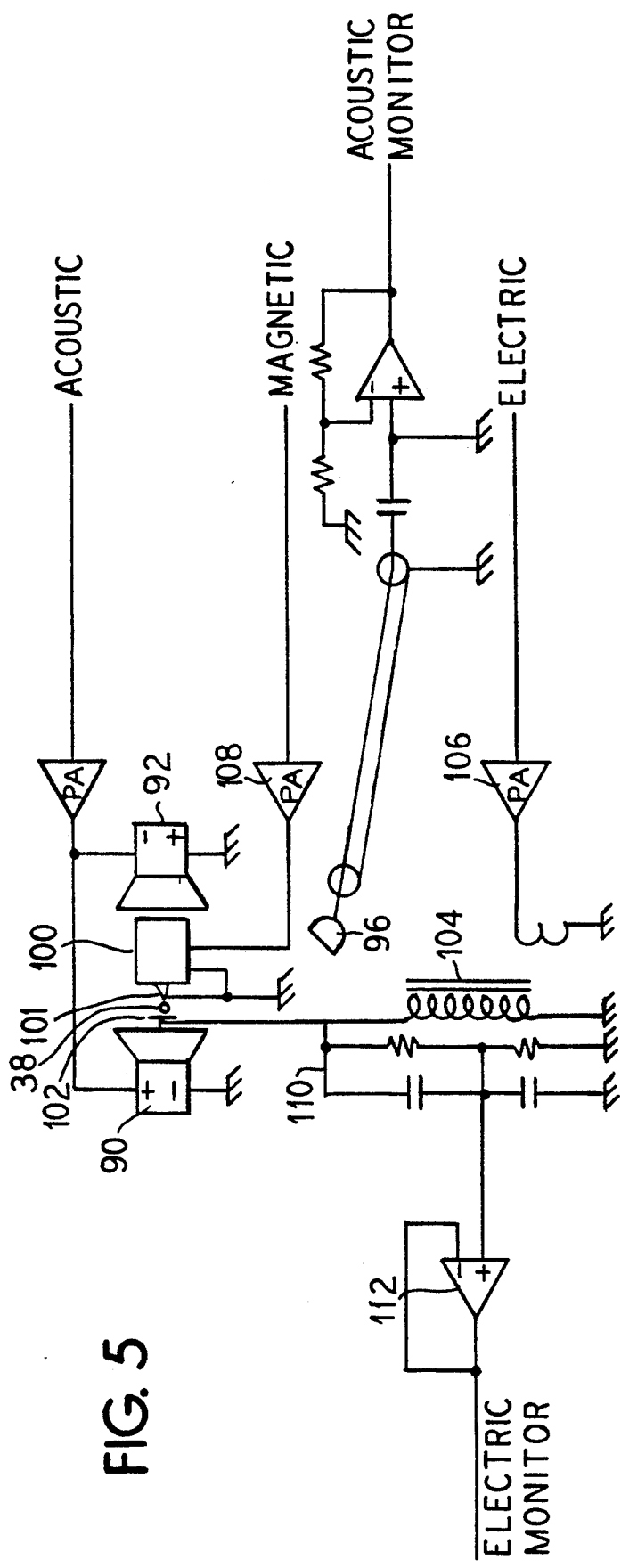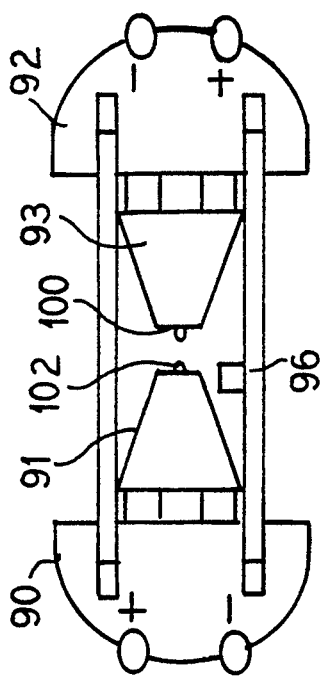
FIG. 5
FIG. 5A
MECHANICAL

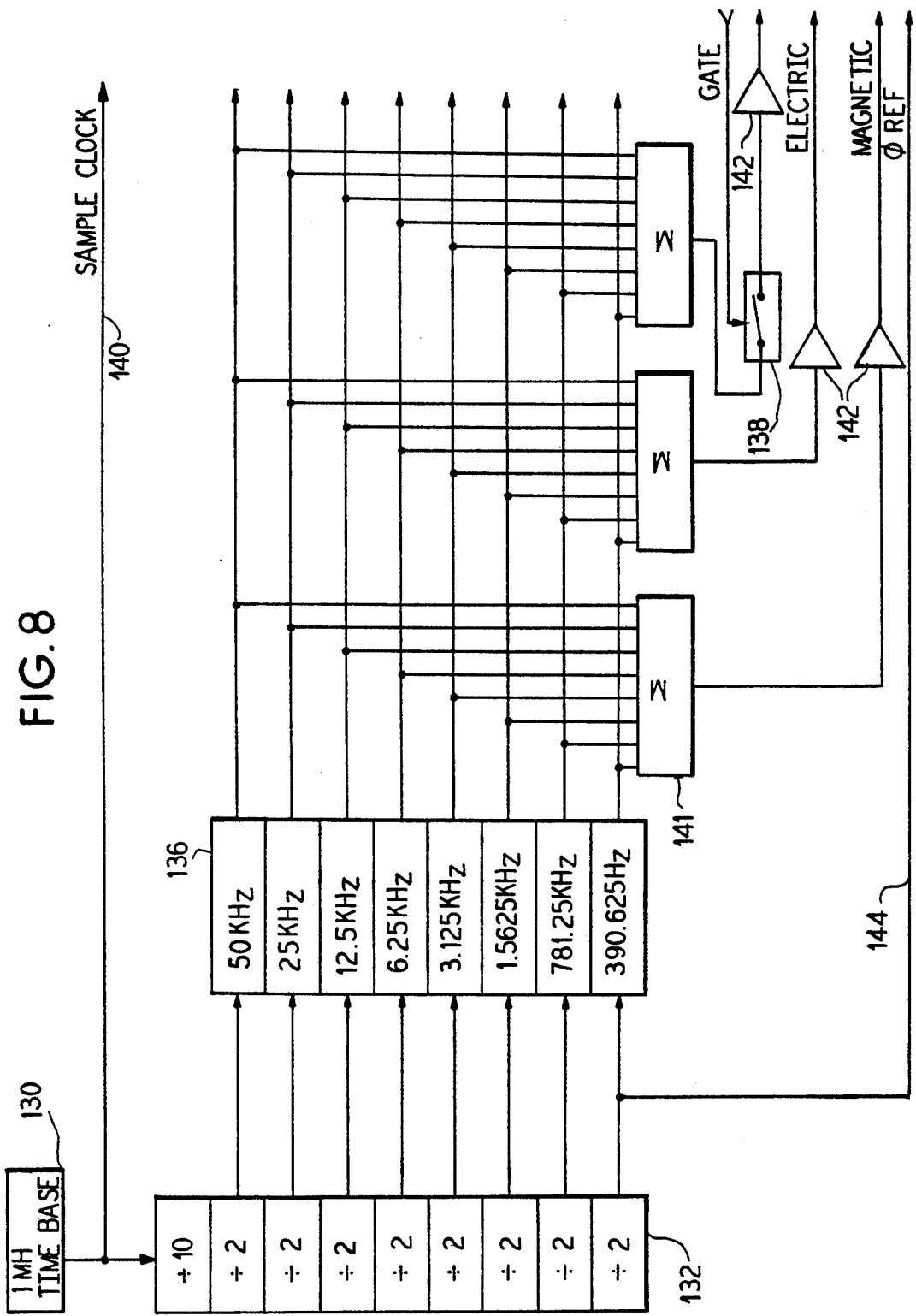

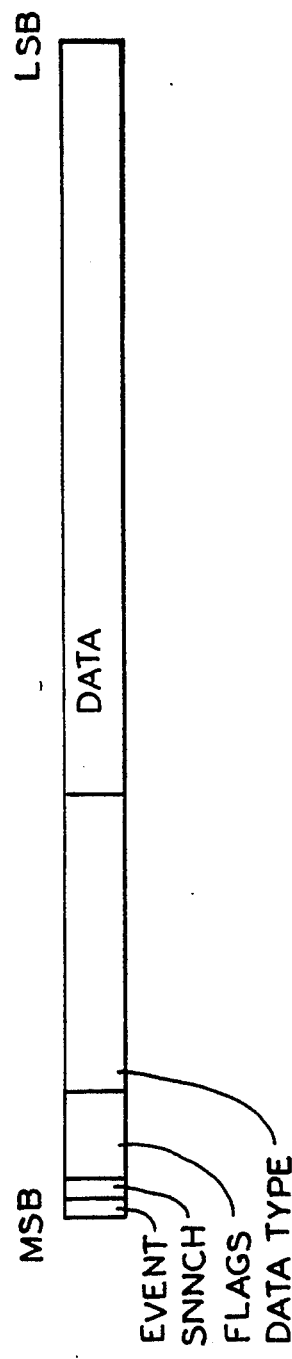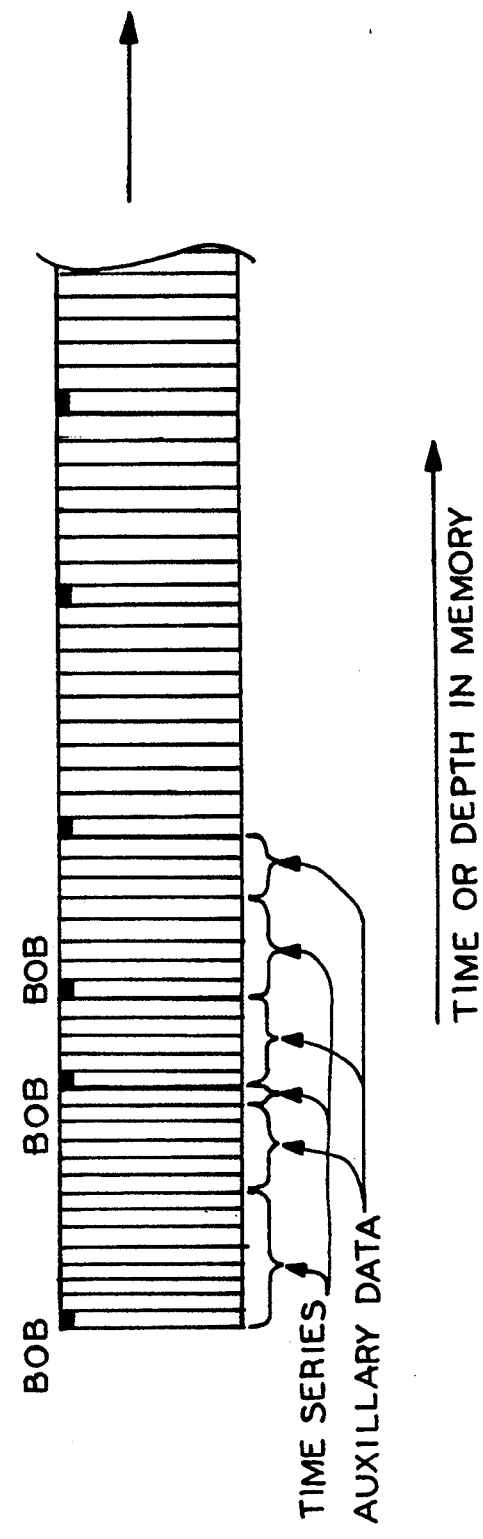

METHOD AND APPARATUS FOR PARTICLE ANALYSIS

BACKGROUND OF THE INVENTION

1. Field of the Invention

The present invention relates to a method for automatically conducting single particle experiments which includes subjecting the particles to external forces, using laser Doppler velocimetery to monitor the motion of the particles, summarizing the particle response to a database, analyzing the information contained in the database and, thus, determining physical properties of the particles in a sample. These physical properties may include particle size, density, charge, magnetic moment and various optical scattering attributes.

2. Description of the Related Art

This and other forced motion particle measurement schemes are descendants of R. A. Milikan's oil drop experiment of 1911. The original experiment exposed small particles simultaneously to gravitational, viscous and electrical forces. By direct observation, the settling velocity and the electrical migration velocity of single particles was measured. Data were interpreted using Stokes law and Coulombs law to yield the aerodynamic diameter and the electric mobility of the individual particles. Many extensions and improvements of the Milikan cell have been used in both experimental physics and in analytical instruments for fine particle assay.

Forced motion experiments other than those involving electricity and gravity make use of acoustic force, magnetic force and fluid gradient forces. Instruments such as the TSI Aerodynamic Particle Sizer (available from Thermo Systems Inc., Minneapolis, Minn.), the Malvern Aerosizer (available from the Malvern Instruments Ltd., Malvern, U.K. are in this category.

Historically, the most important document on the acoustical aerosol sizing technique is Gucker and Doyle, "Amplitude of Vibration of Aerosol Droplets in a Sonic Field", Journal of Physical Chemistry, vol. 60. pp 989-996, (1956). In conclusion, the authors describe an instrument which would use the combination of a linear gradient filter and a photomultiplier tube to accomplish the transduction of particle velocity into an electrical signal. Further description suggests that the velocity magnitude may be processed by "a rapid electronic circuit to obtain the combined count and size distribution, while the phase lag of the particle also could be studied with a rapid electronic phase meter".

The use of LDV (laser Doppler velocimitry) to implement the acoustical sizing technique was first described by Kirsch and Mazumder, "Aerosol Size Spectrum Analysis Using Relaxation Time Measurement", Applied Physics Letters, Vol. 26, No. 4, 15 Feb. 1975. U.S. Pat. No. 4,663,741 discloses an extension of this method for performing simultaneous charge and size measurements in which a combination of an acoustic field and a static electrical field are used.

Sasaki and Sato in "Laser Doppler Particle Measurement Using Forced Vibrations and Power Spectral Analysis", Appl. Optics, Vol. 17, no. 2, pages 230-234 (Jan. 15, 1978), and in "Simultaneous Determination of Particle Size and Density by LDV", Appl. Optics, Vol. 19, no. 15, pages 2565-2568 (Aug. 1, 1980) describe some improvements to the LDV assisted acoustic motion technique. Wilson and Liu in "Aerodynamic Particle Size Measurement by Laser-Doppler Velocimetry", Journal of Aerosol Science, Vol. 11, pp.139-150 (1980), review other previous work in this field pertaining to LDV assisted forced motion. In all cases the LDV system is used to replace the eye or camera used in early work. The experimental formats were formulated before the advent of lasers and hence LDV. Examples of prototype single particle instruments are referenced in N. A. Fuchs, Mechanics of Aerosols, Dover (1964). Experiments involving combinations of alternating electrical fields, magnetic fields, gravity, thermal gradients and acoustic forces are all described and referenced therein.

So far this discussion has omitted an important class of optical particle sizing instruments: Those which use the magnitude and spatial distribution of scattered light to estimate particle size. An excellent summary of the history of this class is to be found in Milton Kerker, The Scattering of Light, Academic Press (1969). With regards to the current invention, the reader is directed to Son and Giel, "Circuit for Simultaneous Measurements of Particle Sizing Interferometer Signal Characteristics", Review of Scientific Instruments, Vol. 58 Number 3, pages 393-400 (1987) and Bachalo's U.S. Pat. No. 4,854,704, for a review of similar art.

SUMMARY OF THE INVENTION

The present invention simultaneously measures a wide variety of physical properties of single particles in a aerosol suspension. New features of the invention allow one or more of the following:

- Detection of valid signals based upon Doppler information alone.
- Detection of optical scattering parameters over a broad dynamic range.
- Rejection of coincidence events, and hence certainty that the measurements made apply to only single particles and not to ensembles.
- Measurement of the time history of the Doppler signals on a very short time scale.
- Multiple measurement modes, for instance, the size, charge, density, magnetic moment and the scattering properties of single particle may be measured simultaneously.
- Several types of self calibration based on relationships between various data items in the data base.
- Control of the flow/sampling system in response to sampling conditions which increases versatility in dry powder analysis and offers some control over the relative sampling efficiency on a sample by sample basis.
- Minimal sampling bias, especially for highly charged particles due to use of a net applied force that has zero mean over time.
- Sound field stabilization and monitoring which reduces the need for repeated calibration.

BRIEF DESCRIPTION OF THE DRAWINGS

FIG. 5 is a schematic diagram of a various transducer arrangements for the present device;

FIG. 8 is a block diagram of a stimulus generator for transmitting stimulus signals to the transducers;

FIG. 17 is a diagram of the burst data format used in the data reduction process.

DETAILED DESCRIPTION OF THE PREFERRED EMBODIMENTS

Physical Principles

Figure 1:
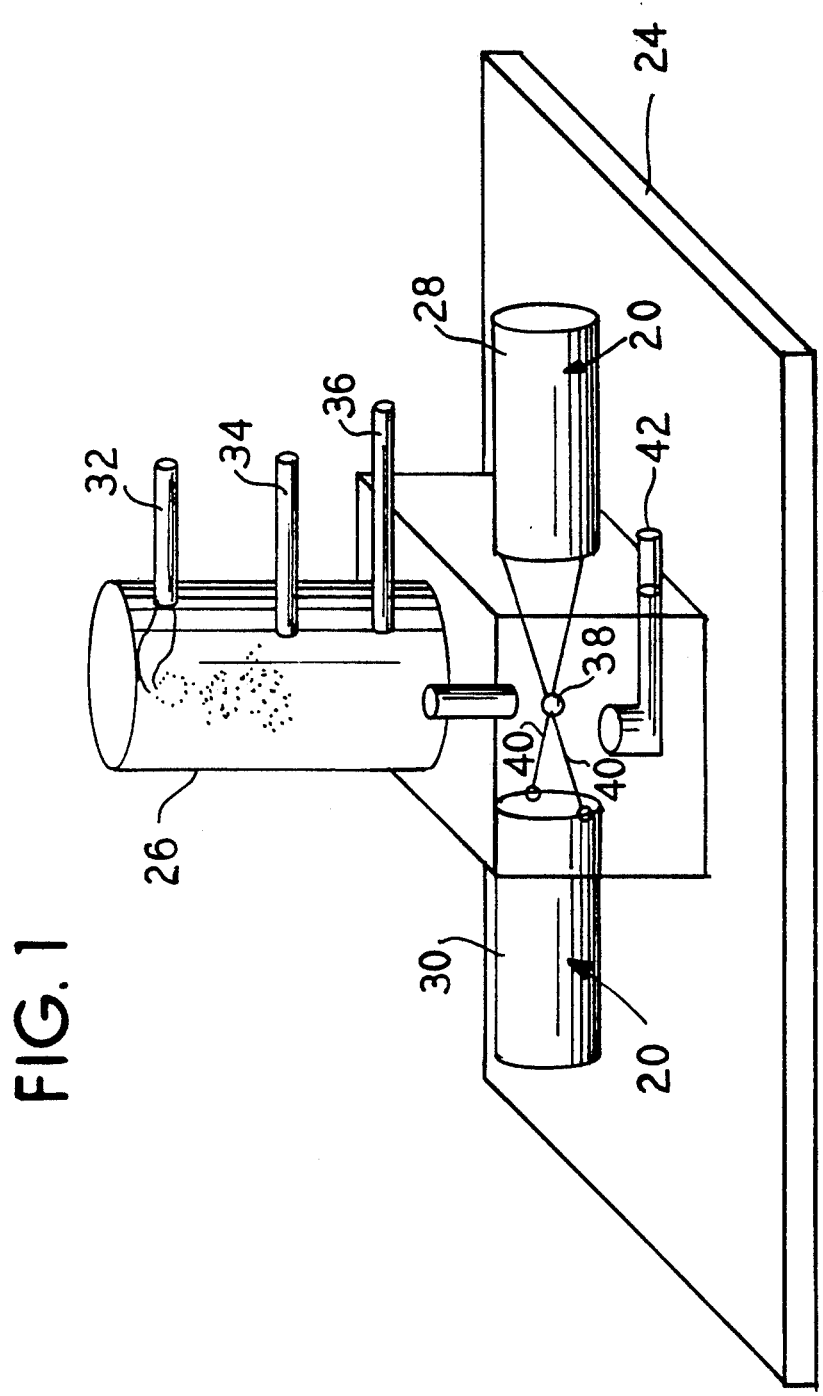
FIG. 1 is a perspective view of a laser Doppler velocimeter and associated apparatus for particle analysis according the principles of the present invention.

The technique of forced motion particle measurement uses the response of particles to external forces to determine the physical attributes of the particles under test. A number of well known instruments make use of this principle. Accounts of prototype instruments are referenced in Fuchs (see above).

Stokes law governing the steady state motion of spheres in a viscous fluid is the basis of most forced motion particle measurements. However, Stokes law is not sufficient when the particles in question are subject to acceleration. Here the inertial force due to the displacement of the fluid by the particle becomes significant. Displacement effects increase as the volume of the particle in question increases and are greater for less dense materials. The Basset-Bosinesq-Oseen equation (as shown in the Fuchs reference) is a useful mathematical model for non-steady rectilinear motion. Solutions of the B-B-O equation for various applied forces are referenced by Fuchs and the following expressions are taken from this reference. Small particles are also subject to molecular slip so an adjustment may be made in the value of viscosity used in calculating the particle response: Allowing $\eta'$ to equal $\eta/C_c$, where $C_c$ is the Cunningham slip factor approximated by $1+\alpha K_n$, $\alpha$ is a property of the gas/particle interface (typically 1.24 for an air oil interface) and $K_n$ is the Knudsen number relating the size of the particle to the mean free path of the molecules in the gas. Various groups and dimensioned quantities found in these solutions are as follows:

$$\beta = \frac{2}{d}\sqrt{\frac{2\eta}{\omega\rho_p}}, f = \frac{2\rho_p}{3\rho_g}, \tau = \frac{d^2\rho_p}{18\eta}$$

Where $\eta$ is viscosity, $\rho_p$ is particle density, $\rho_g$ is gas density, $\omega$ is angular frequency of the applied force, and $d$ is particle diameter. $\tau$ is relaxation time and $\beta$ and $f$ are dimensionless groups. This is significant since the number of dimensioned attributes which may be determined is related to the number of known constant attributes and the number of groups contained in the solutions.

If the force applied to the particle is continuous and the particle is in equilibrium, then the following equations may be used to determine the steady state velocity $V_s$.

$$V_s = \frac{\tau}{m} F_s$$

This equation is known as Stokes law, where F is force and V is particle velocity. If the force is gravity, $V_s$ is the settling velocity and only the diameter square root density product may be obtained. This product referred to as the aerodynamic diameter is a useful particle parameter even if the density of the particle is unknown. Stokes law applies only to steady motion of a particle in response to a static applied force.

The solution of the equation of motion for a sphere in a sound wave is given by the equations:

$$V_a = \sqrt{\frac{1 + 3\beta + 9/2\,\beta^2 + 9/2\,\beta^3 + 9/4\,\beta^4}{f^2 + 3f\beta + 9/2\,\beta^2 + 9/2\,\beta^3 + 9/4\,\beta^4}}$$

$$\phi_a = \tan^{-1}\left(\frac{3/2\,(f-1)\,\beta\,(1+\beta)}{f(1 + 3/2\,\beta) + 3/2\,\beta + 9/2\,\beta^2 + 9/2\,\beta^2 + 9/2\,\beta^3 + 9/4\,\beta^4}\right)$$

Note that these equations are in polar form, but may also be expressed as a complex pair for $V_a$.

For sinusoidally varying external forces such as electrical or magnetic forces ($V_e$) the solution is expressed by the following equations.

$$V_e = \frac{F_e}{\omega m \sqrt{f^2 + 3\beta f + 9/2\,\beta^2 + \beta^3 + 9/4\,\beta^4}}$$

$$\phi_e = \tan^{-1}\left(\frac{2/3\,f + \beta}{\beta\,(1+\beta)}\right)$$

Note that the phase part of the solution is a function only of particle diameter and density (if the system attributes are constant) while the magnitude is a function of diameter, density and the qE product (in the case of an electrical force $F_e$).

The above solutions may be interpreted as transfer functions and as a consequence, control system theory may be brought to bear. To rephrase this, the particle velocity $V_p$ is the product of a potential velocity and a dimensionless complex function. In the above equations, terms $\beta$ and f define the transfer function and the potential velocity is either the velocity of the surrounding gas or the velocity the particle would obtain under similar force in a vacuum. For several forces applied simultaneously, the following relationship is implied:

$$V_{particle} = V_{steady} + V_{acoustic} + V_{external}$$

That is, since the system is linear, the total response is equal to the sum of the responses due to each force acting independently. If the functions controlling the forces are orthogonal in time or space, the resulting particle motion can be decomposed into components due to each force acting independently. For spherical particles, no discrepancies between the linear model and experiment have yet been found.

A simple mathematical model for non-spheres is not available, but it is assumed that any force which could modulate the drag force relative to other applied forces (such as changing the orientation of non-spherical particles during the course of measurement) might result in measurably non-linear behavior. Harmonic products would then be present in the spectrum of motion and it can be assumed that such phenomena could be useful in the classification of non-spheres. Present technique allows this type of measurement even though the analysis is unavailable.

In the case of acoustic force, it is possible to solve the system of equations $\phi(\beta,f)$, $V(\beta,f)$ to yield an unambiguous solution in $\beta$ and f. Since the constituent variables in $\beta$ and f ($\omega$, $\eta$ and $\rho_g$) are known, particle density $\rho_p$ and particle diameter d may be determined independently. After density and diameter are determined, other components of particle motion may be examined to determine the electrical charge nq (since electrical force is equal to the nqE product and E is controlled) or the charge/assumed mass ratio (if the density cannot be accurately determined). The magnetic moment/field product ($\mu B$) is similarly determined.

Figure 13:
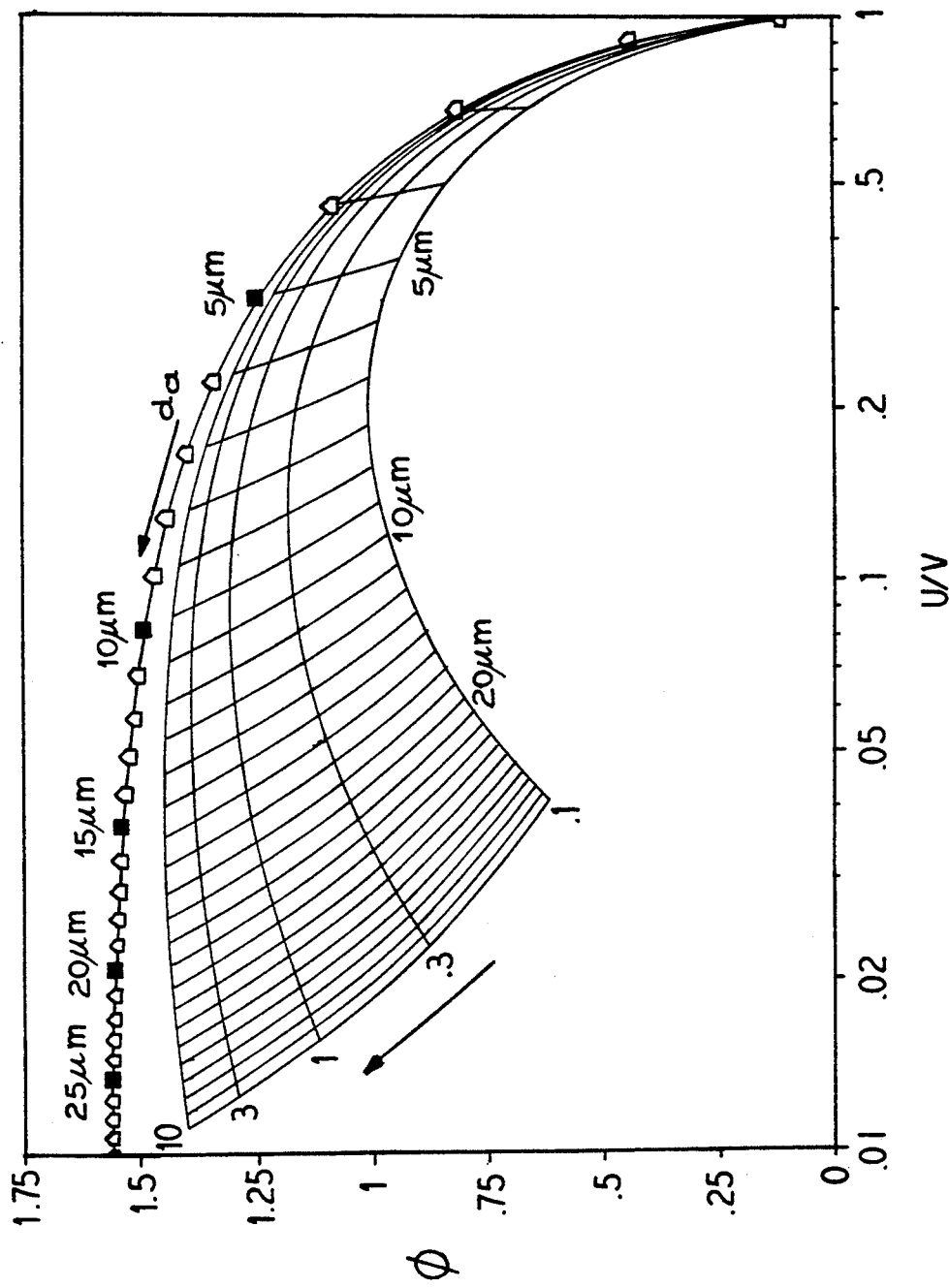
FIG. 13 is a plot of the response of particles of varying density and diameter in air at STP to an acoustic wave of 6250 Hz.
Figure 14:
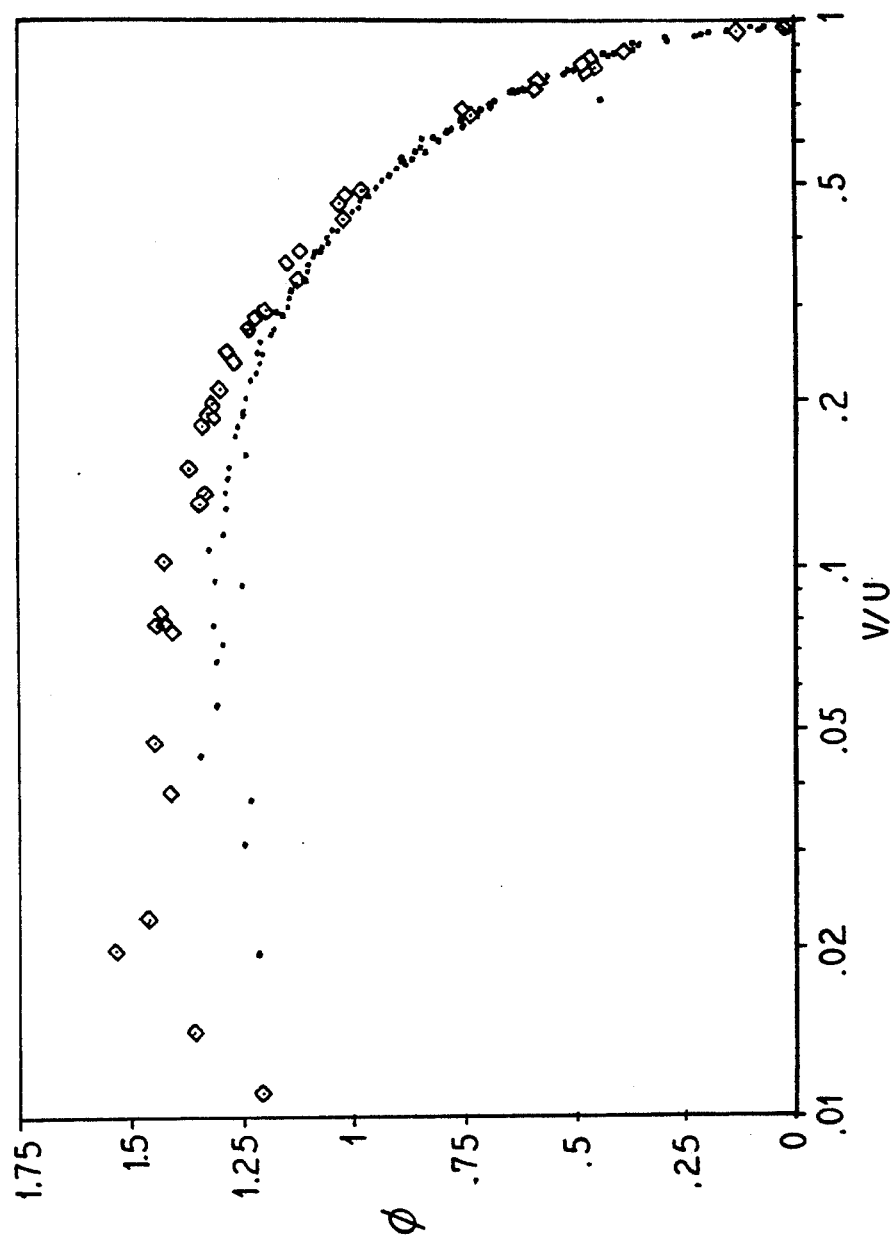
FIG. 14 is a plot of the measured response of test particles under going acoustic motion at 6250 Hz.
Figure 15A:
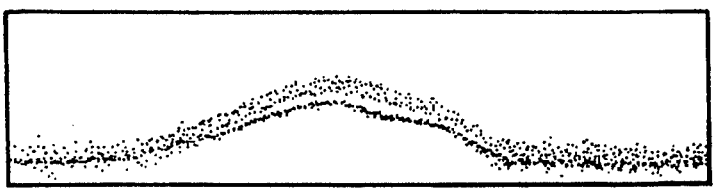
FIGS. 15a to 15p are a plot of the measured response of several particles with the computed summary data superimposed on the plots.
Figure 15B:
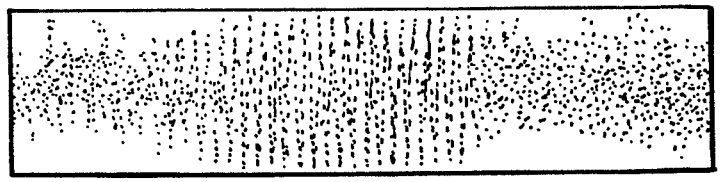
Figure 15C:
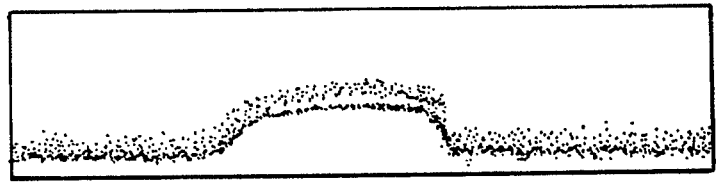
Figure 15D:
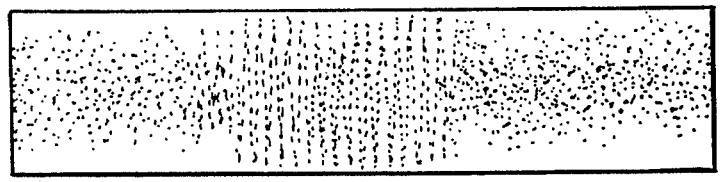
Figure 15E:
Figure 15F:
Figure 15G:
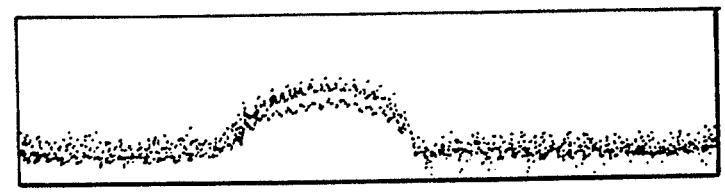
Figure 15H:
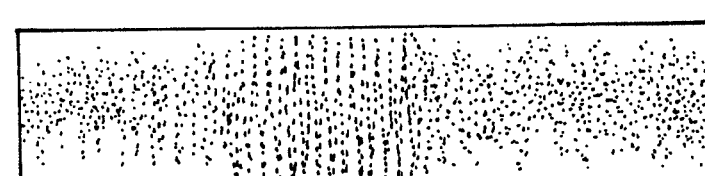
Figure 15I:
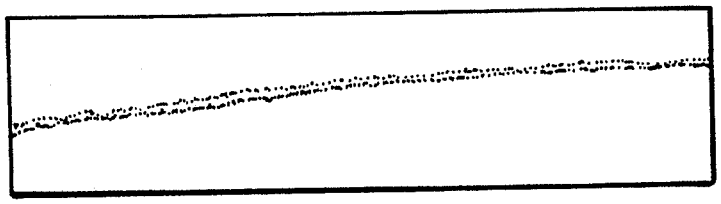
Figure 15J:
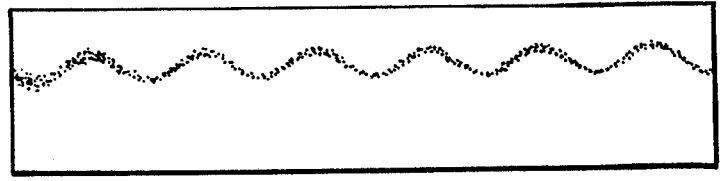
Figure 15K:
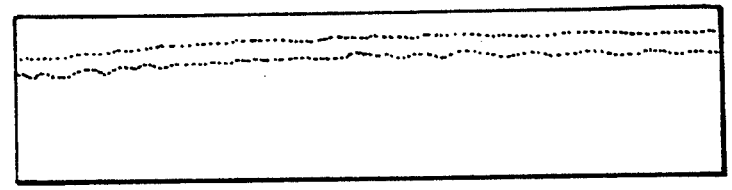
Figure 15L:
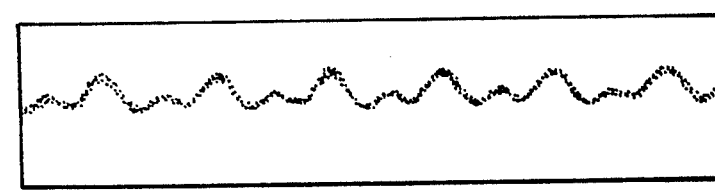
Figure 15M:
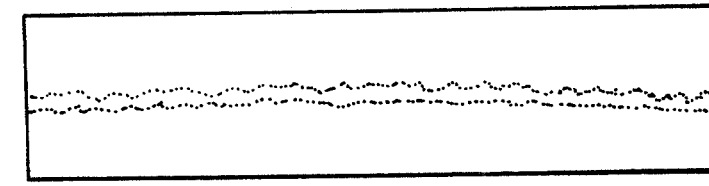
Figure 15N:
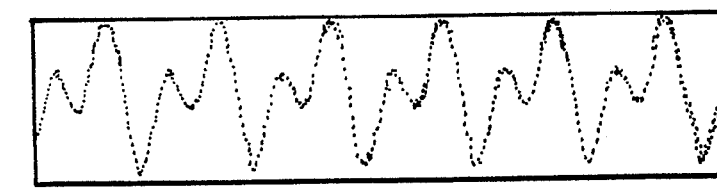
Figure 15O:
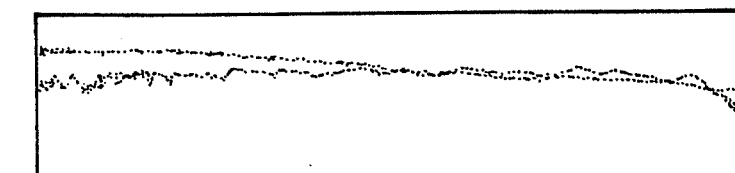
Figure 15P:
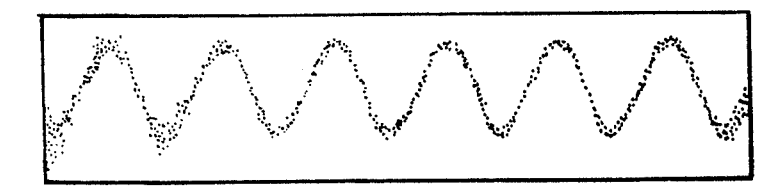

A plot of the acoustic response function $\phi_a(\rho,d_a)$ verses $V_a((\rho,d_a)$ evaluated at 6250 Hz is given in FIG. 13. Note that the lines of constant density are orthogonal to those of constant aerodynamic diameter, and are especially distinct for larger sizes. The aerodynamic diameter $d_a$ is the physical diameter times the square root of the density. There are several other noteworthy features of this graph. The maximum phase shift on a given curve is a function of density and a function of the velocity ratio or, in this case, the log of the relative particle velocity. By way of comparison, an actual response of a heterodisperse test aerosol is shown in FIG. 14. These observations figure prominently in the self-calibration schemes to be described hereinafter.

Apparatus

Practice of this invention requires: 1) a frequency biased differential laser Doppler velocimeter (LDV) optical system, 2) a processor for the signals originating in the LDV system, 3) means of generating and controlling forces applied to particles, 4) means of delivering a sample to the measurement system, 5) a data acquisition, control system to integrate the other components into a workable instrument, and 6) a general purpose computer to analyze the resulting database.

Experimental formats which may be readily automated by this method include tests in which particle motion is caused by: 1) a single force applied along a single axes, 2) several forces acting along a single axis, and 3) multiple forces acting along either of two axes. The forces used determine the nature of the particle attributes which can be measured. Dual axis formats require that an optical system supporting this type of measurement be used and that a second Doppler processor is used to extract scattering and motion signals from the second optical channel.

In FIG. 1 is shown an overall arrangement of the apparatus. This particular configuration is illustrative of the technique as applied to powder assay. The active region or sensing volume 38 of the apparatus is formed by the crossing of two or more laser beams 40, one of which is frequency shifted relative to the others, emitted from the transmitting optics 28 and thereby producing a region of moving light and dark bands caused by interference of the coherent light of the laser beams 40.

In the case of a two axis system, two moving patterns are formed, each having a distinct color or polarization state. The two patterns are directionally orthogonal and the signals originating from each axis are separated by a color or polarization selective beam-splitter at the receiving optics. As the aerosol particles pass through the sensing volume 38, they scatter light from the moving fringe, or interference, pattern. This scattered light is detected by receiving optics 30, which includes a photomultiplier tube which converts the light signal into an electrical signal. This arrangement is known generically as a frequency shifted differential laser Doppler velocimeter or LDV for short and is widely used in gas dynamic studies. One characteristic of differential LDV is that the vector along which the velocity is sensed is determined by the transmitting optics alone and not by the location or placement of the receiver.

The LDV, flow system and auxiliary equipment are mounted on a platform 24. Auxiliary equipment includes an environmental housing 22, above which is mounted a sample preparation chamber 26. The LDV optics are mounted so that the active LDV sensing volume is within the environmental housing 22. In the case of a single axis system, the LDV is set up so that the sensing vector and the viewing angle may easily adjusted so that the velocity of particles may be measured in a vertical as well as a horizontal direction. In the sample preparation chamber 26 is situated a blow off cup or other means of dispersing a particle sample for analysis. The aerosol particle sample is carried into the sample preparation chamber 26 through an inlet tube 32. A diluent gas may be injected via a tube 34 so that aerosol concentration is reduced sufficiently that, on average, only one particle passes through the sensing volume 38 at a time. Depending on the sample to be tested, an atmosphere other than air may be desired, such sulfur hexafluoride or dry nitrogen. For this reason, the environmental housing 22 may be sealed. During a dilution cycle, waste gas is removed Via outlet tube 36. The prepared aerosol sample is pulled through a sample tube 38 into the environmental housing 22 in a direction toward the sensing volume 38. Once the particle laden gas has passed through the sensing volume 38, it passes out of the environmental housing 22 via a waste tube 42.

External forces are applied to the sensing volume 38 to effect the particle movement, these external forces possibly including static and/or varying electrical fields, static and/or varying magnetic fields, and/or an acoustical field is applied in different combinations as desired. Gravitational and thermal forces are also unavoidably present and also may be used to perform particle measurements by the disclosed means. External forces are applied by transducers which, for example, are located opposite one another on either side of the sensing volume 38. Other arrangements may include single transducer or transducers arranged along a horizontal axis or a vertical axis. In all cases, the LDV sense vector defines the direction in which the particle motion due to the applied forces will be sensed.

Figure 18:
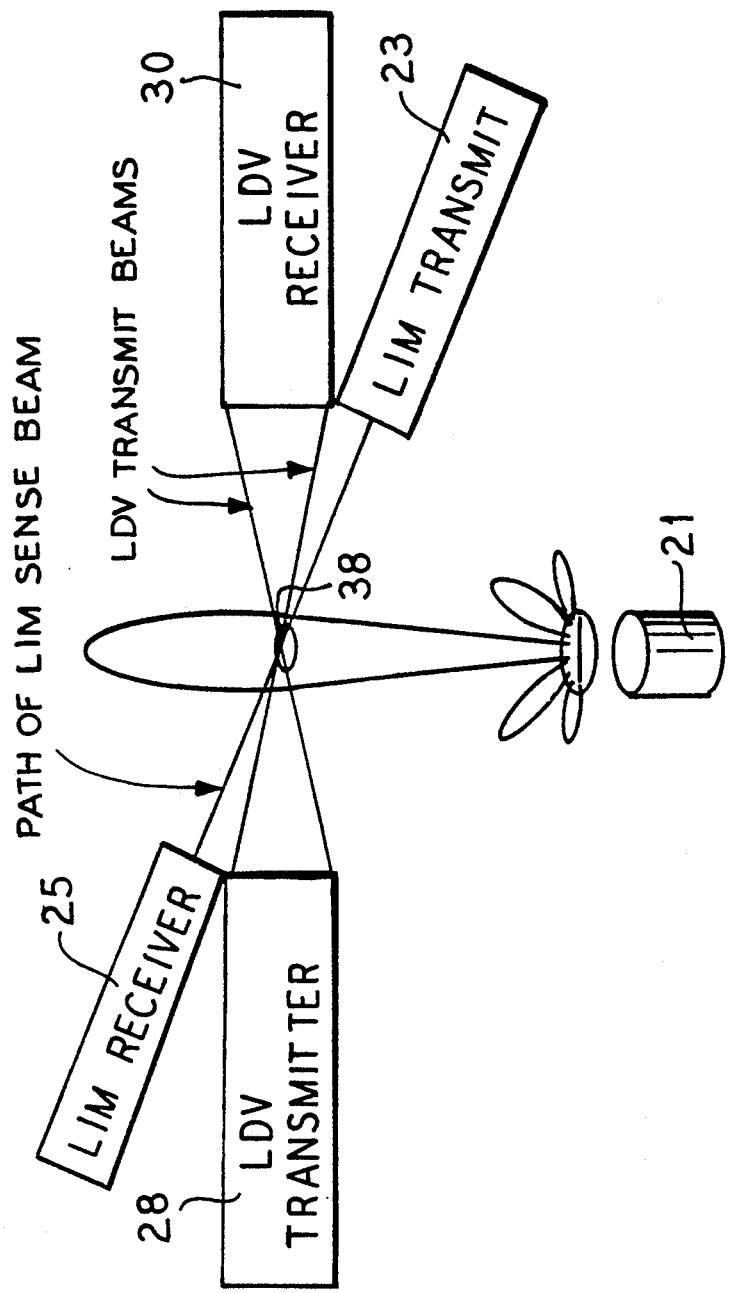
FIG. 18 is a perspective view of the apparatus assembled for the practice of remote sensing.

FIG. 18 shows a configuration of apparatus used to apply this technique to remote sensing. The only force used in this application is acoustic and no environmental housing or flow system is used. Provision is made for monitoring the acoustic field. The LDV transmitter 28 and receiver 30 are some distance apart. The acoustic field is generated by a high power, directional source 21 and sensed by a laser interference microphone whose components are a transmitter 23 and a receiver 25. Any acoustic source used in this work should be capable of producing an acoustic velocity of 0.1 m/S or greater at the sensing volume. The sensing volume 38 may be a meter or more away from any surfaces if sufficient laser power is available for the LDV system.

Figure 2:
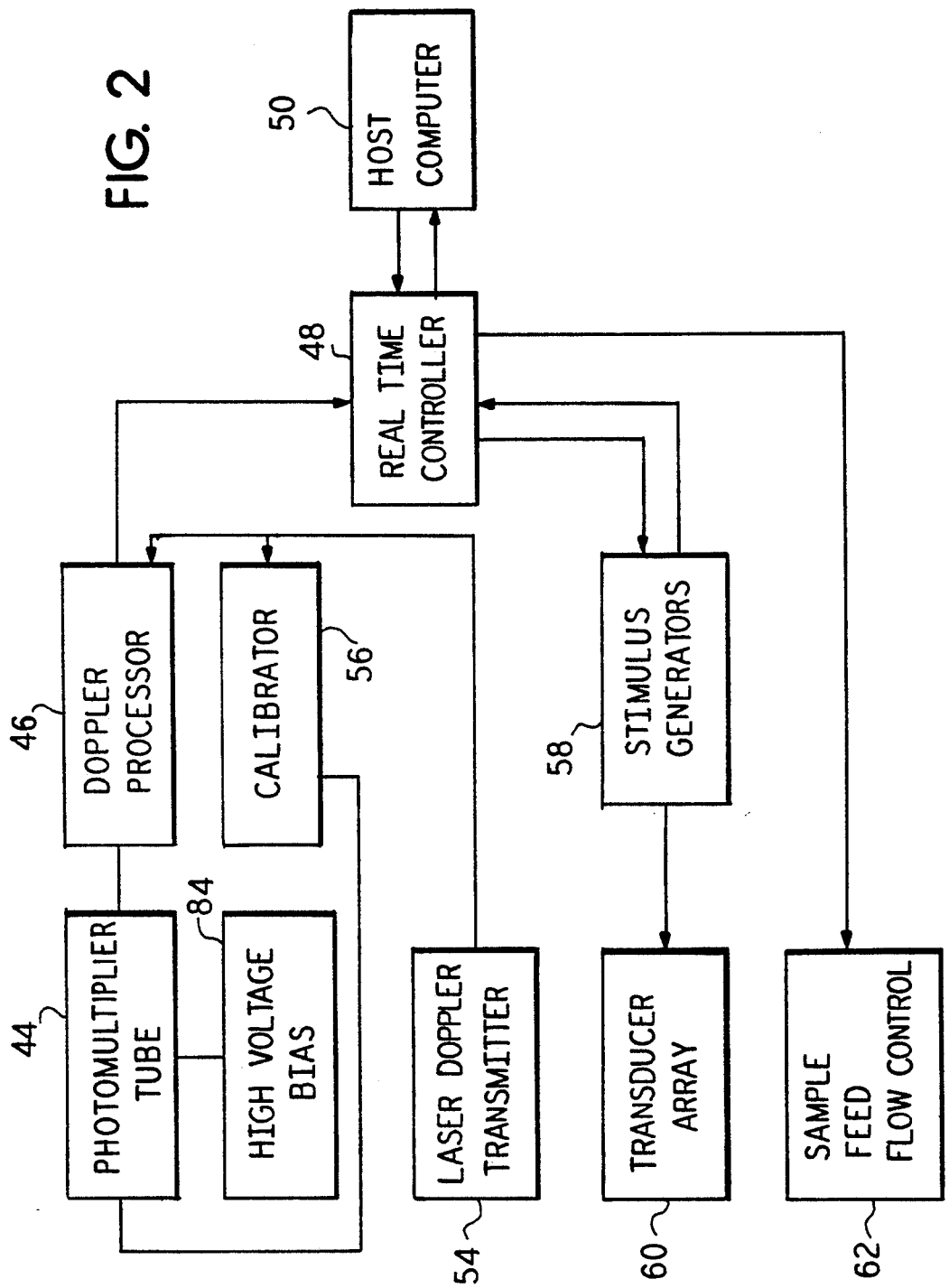
FIG. 2 is a block diagram of the overall control and processing circuitry according to the present invention.

FIG. 2 is a functional block diagram showing the communications paths between various components of the apparatus. A photomultiplier tube 44 is used as a detector by the laser Doppler receiver. The detected photo-current is input to a Doppler processor 46. A host computer 50 accumulates a summary database and may be connected to exert control over other components. A stimulus generator 58 generates signals which drive a transducer array 60. The transducers produce external force fields which act on the particles under test. A real time processor 48 generates event triggers, controls the flow of data into the host computer, formats the data and inserts time and record marks. The controller 48 also communicates with the stimulus generators and the flow/sample system. This allows the applied stimulus to be altered in response to individual particles and allows control of the sample feed and flow control means 62. The stimulus generators 58 also supply a reference signal to the controller 48 so that phase of at least the fundamental component of the stimulus is known to the host computer.

Doppler Processor

Figure 3:
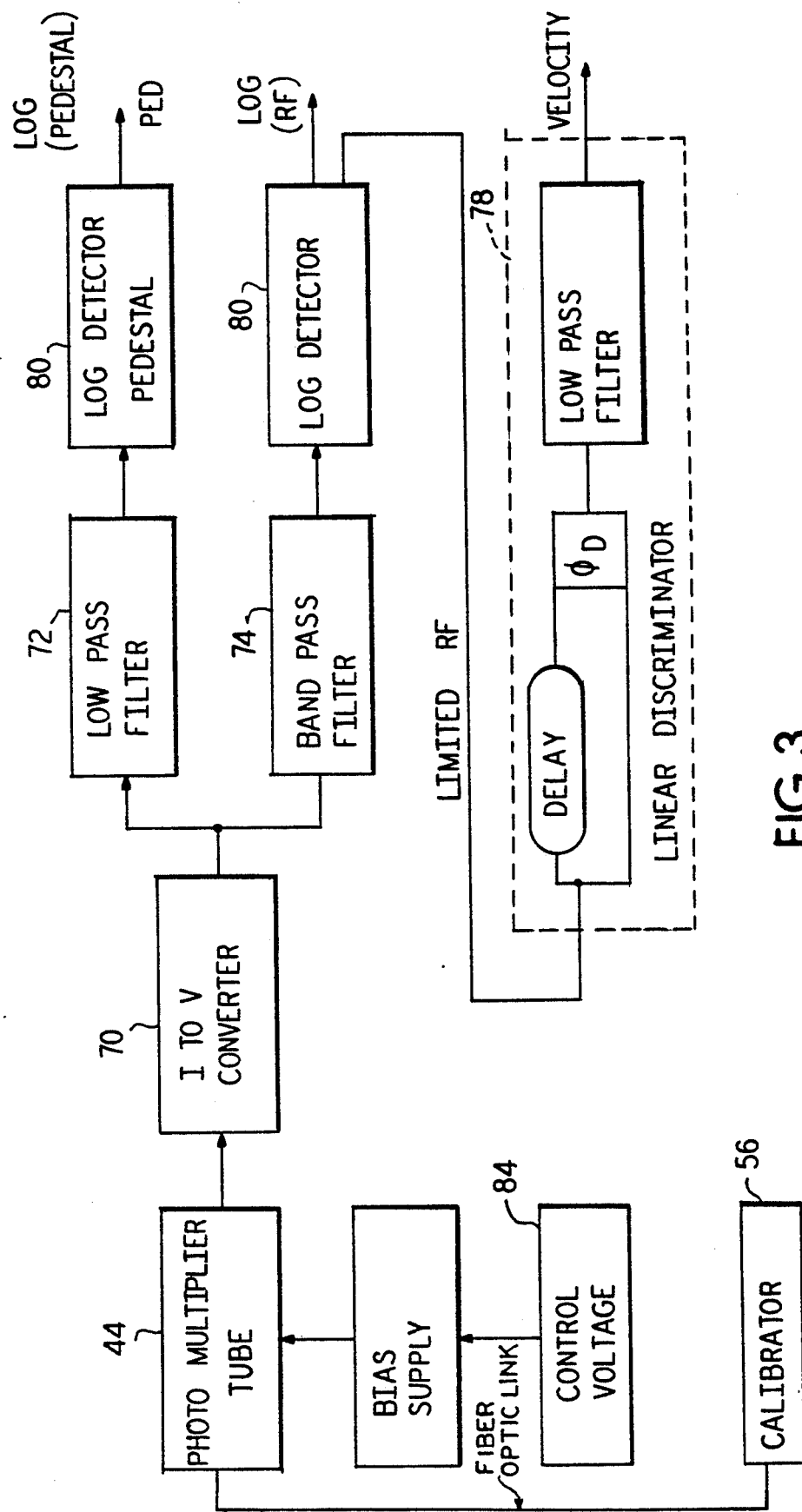
FIG. 3 is a block diagram of the Doppler processor of the present device.

Referring to FIG. 3, light scattered by particles passing through the sensing volume 38 is detected by the photomultiplier tube 44 to generate a current, the current being transformed to a voltage by a current-to-voltage converter 70. The voltage output of the converter 70 is divided into two channels through a low pass filter 72 and a bandpass filter 74. The bandpass filter 74 has a well defined bandwidth and a center frequency, both of which are independently adjustable. The amplitude of the bandpass component is detected in a logarithmic detector 76 to produce a signal proportional to the logarithm of the RF component of the scattered light. Amplifiers of this type also double as RF limiting amplifiers so that, in addition to the detected output, a constant amplitude, limited RF signal is available from this device. A signal proportional to the particle velocity is produced by feeding this limited RF signal to a linear discriminator 75, which produces a signal proportional to the particle velocity. An exemplary version of this discriminator divides the limited RF signal into two paths, one of which is delayed by a delay line 77. These two signals are then processed by a phase detector 78 and a low pass filter 79 to produce a signal which is linearly proportional to the short term Doppler frequency. The RF processing may also include frequency translation stages to ease the performance requirements of the bandpass filter and the frequency discriminator. In this case, all local oscillator signals are derived from the LDV transmitter so that drift is minimalized.

The signal from the low pass filter 72 is likewise fed to a logarithmic amplifier strip 80 to produce a signal proportional to the logarithm of the low pass, or Pedestal, component of the scattered light. The limiter output of this channel is unused. The photomultiplier 44, the bandpass filter 74 and the frequency discriminator 75 are calibrated according to the present invention by a calibrator 56. Both logarithmic detectors 76 and 80 are, for example, Analog Devices model AD 640, which are DC coupled, temperature compensated, and trimmed to provide excellent log linearity. In summary, the input of the Doppler processor is the detected current taken from the photomultiplier tube or tubes PMT(s) 44 in the LDV receiver. The outputs are termed PED (the logarithm of the low frequency component of the LDV signal), RF (the logarithm of the radio frequency component of the LDV signal) and VELOCITY (which is analogous to the velocity of a particle in the sensing volume of the LDV system when a particle is present or which is wide-band noise otherwise). Subsequent processing determines the validity of these signals and extracts other information from the validated segments.

Calibration of Doppler Processor and PMT

Figure 9:
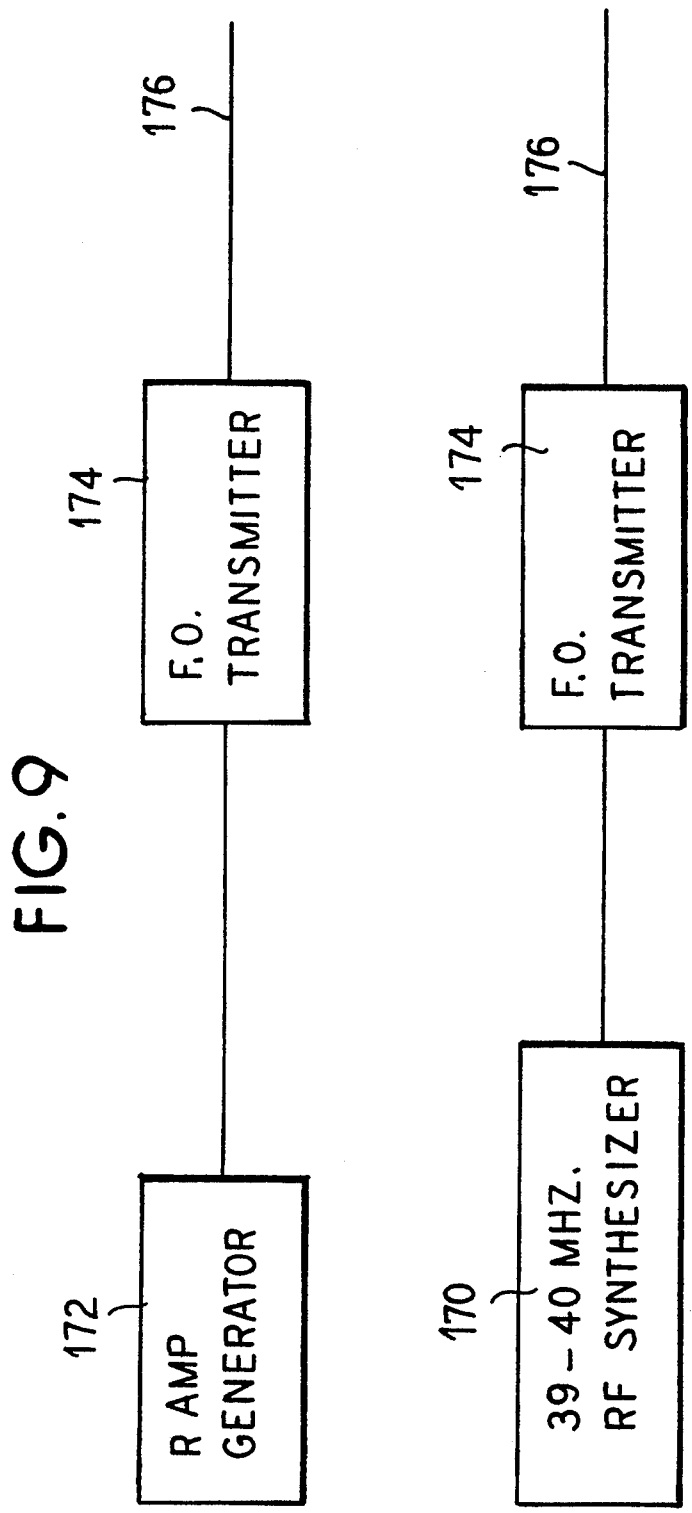
FIG. 9 is a block diagram of a calibration system for calibration of the photomultiplier tube according to the present invention.

The frequency discriminator of the Doppler processor and the photomultiplier tube (PMT) 44 are calibrated using the circuit shown in FIG. 9. This device generates optical test signals which are delivered to the PMT 44 housing by optical fiber cables 178 and 179. A synthesized RF source 170 having a tuning range which corresponds to the working frequency of the discriminator is used to supply a signal to a suitable fiber optic transmitter 171. The other fiber link 179 is attached to a fiber optic transmitter 173 driven by a ramp generator 172. By sequentially tuning the RF source and simultaneously monitoring the velocity signal, the linearity and conversion gain of the discriminator in the Doppler processor can be measured. It is assumed that the LDV beam intersection angle and the laser wavelength(s) are known, so the particle velocity is easily computed once the calibration is performed. To insure repeatable, stable operating conditions, the PMT 44 should be calibrated regularly. This calibration also allows the system to function as an optical particle sizer without the need for a calibration standard.

In an ideal photomultiplier tube with gain $A_i$ the noise current may be computed:

$$I_n = \sqrt{2qA_iI_aB}$$

where $A_i$ is the current gain, $I_n$ is the noise current, q is the elementary charge, B is the bandwidth, and $I_a$ is the anode current. The two logarithmic detectors in the present apparatus produce signals which represent the logarithms of short term mean current, or pedestal, and fringe current, or RF. The bandwidth of the RF channel is set by a filter with an adjustable bandwidth and center frequency. The gain of the photomultiplier tube as a function of applied voltage is given by the formula:

$$A_i = K_1 V^{k_2}$$

wherein $A_i$ is the current gain, V is the bias voltage, $K_2$ is related to the number of stages, the emissivity, etc., and $K_1$ is related to the collection efficiency and the first stage performance. $K_1$ includes a factor F, which is a noise factor, which causes an over-estimation of the gain. Because of this, a new term $A_n$ must be defined:

$$A_n = F A_i$$

wherein $A_n$ is termed the noise gain. If the apparent gain is observed to increase at a given bias voltage, then the factor F is increasing. On the other hand, if a decrease is measured in the gain, $K_2$ is decreasing.

A calibration technique based on these observations follows:

A ramped light source is applied to the photo-cathode, so that the measured anode current ranges from the dark current level to saturation. The inflection points, slope and end points of the RF verses PED curve give the input noise level, optical background and dynamic range of the system at a given bias voltage setting. The curve should have a slope of 0.5 over the linear range of the PMT under test and less towards the noise level and saturation. All subsequent measurements are made within this linear region. Under these conditions, all of the current in the radio frequency band is noise. Thus, $I_n = I_{RF}$. The sampled values of RF and PED are recorded and form a database for subsequent calculations. Applying logarithmic calculations:

$$2Log(I_{RF}) = Log(I_n) + Log(2qB) + Log(A_n),$$

wherein q is the elemental charge. To compute the noise gain, the bandwidth B must be known. The band pass filter 74 determines the center frequency and bandwidth of the RF channel. Filter settings are determined experimentally using the fiber coupled synthesized RF source in combination with the log detector. Values for Log(RF) and Log(Ped) have already been obtained, so that the equation for gain may be written as:

$$Log(A_n) = Log(I_n) - 2Log(I_{RF}) + Log(2qB).$$

Taking measurements at two voltages, it becomes possible to simultaneously solve the equations:

$$A_{n1} = K_1 V_1^{K_2} \text{ and } A_{n2} = K_1 V^{k_2},$$

Thus, the calibration of the PMT 44 is accomplished. $K_1$ and $K_2$ are the coefficients which determine the PMT gain and are computed and stored for reference. If examination of the PMT calibration record shows that these coefficients are changing, then the detection properties of the processor are also affected. This, along with a determination of background photo current, makes it possible to maintain consistent detection limits and counting sensitivity. The reason for this is that FM discriminators are non-linear devices with well defined detection thresholds. The most significant threshold in the present device is the FM improvement threshold, or second threshold. Above this threshold, the time varying components of the demodulated Doppler signal achieve their representative level. Since the FM demodulation process is threshold dependent, no amount of post detection filtering can recover a representative Doppler signal if the input signal-to-noise ratio (SNR) is below the second threshold although estimations may be possible based on the independent measurement of SNR and knowledge of this threshold effect.

The RF noise floor of the RF processor itself is found by increasing the drive current to the fiber coupled from the calibration circuit until the output of the RF detector is increased by 0.3 volts above the dark level, which corresponds to a +6 dB increase since the logarithmic amplifier has a one volt per decade conversion slope.

The input SNR under real conditions is also easily determined:

$$Log(SNR) = LOG(I_{RF}) - \frac{LOG(I_{Ped})}{2} + a \text{ constant}$$

This allows the same principle used in PMT calibration to be used to evaluate signal quality in real time.

It is contemplated that the foregoing cllibration procedure may be applied to all shot noise limited photodetectors.

Trigger Generation

Because of the intensity distribution of the light forming the sensing volume and the nature of the photo-detection process, a typical LDV burst is characterized by a rapid succession of signal conditions as a particle transits the sensing volume. For a given particle, the noise present in the signal itself and the noise in the demodulated signal is always smallest at the center of the transit and relatively larger at the beginning and end of the transit. When no particle is present, only noise is present at both the input and output of the discriminator. Signals should be excluded from processing which are too noisy to yield good velocity signals or which result from various types of multiple scattering conditions. In further discussions, multiple scattering is referred to as coincidence. There are 3 types of coincidence which may be identified by this system: 1) True coincidence, wherein two objects of relatively equal scattering magnitude are simultaneously present in the sensing volume; 2) Near coincidence, wherein large objects transiting the beams outside of the sensing volume scatter enough light to interfere with the detection of a smaller object in the sensing volume; and 3) Serial coincidence, wherein two or more particles sequentially transit the sensing volume with no intervening dead time. All of these coincidence modes are detected by the processing described herein. Type 1 and 2 are typically rejected by the trigger circuits and type 3 is detected by processing on the accumulated database.

Figure 4:
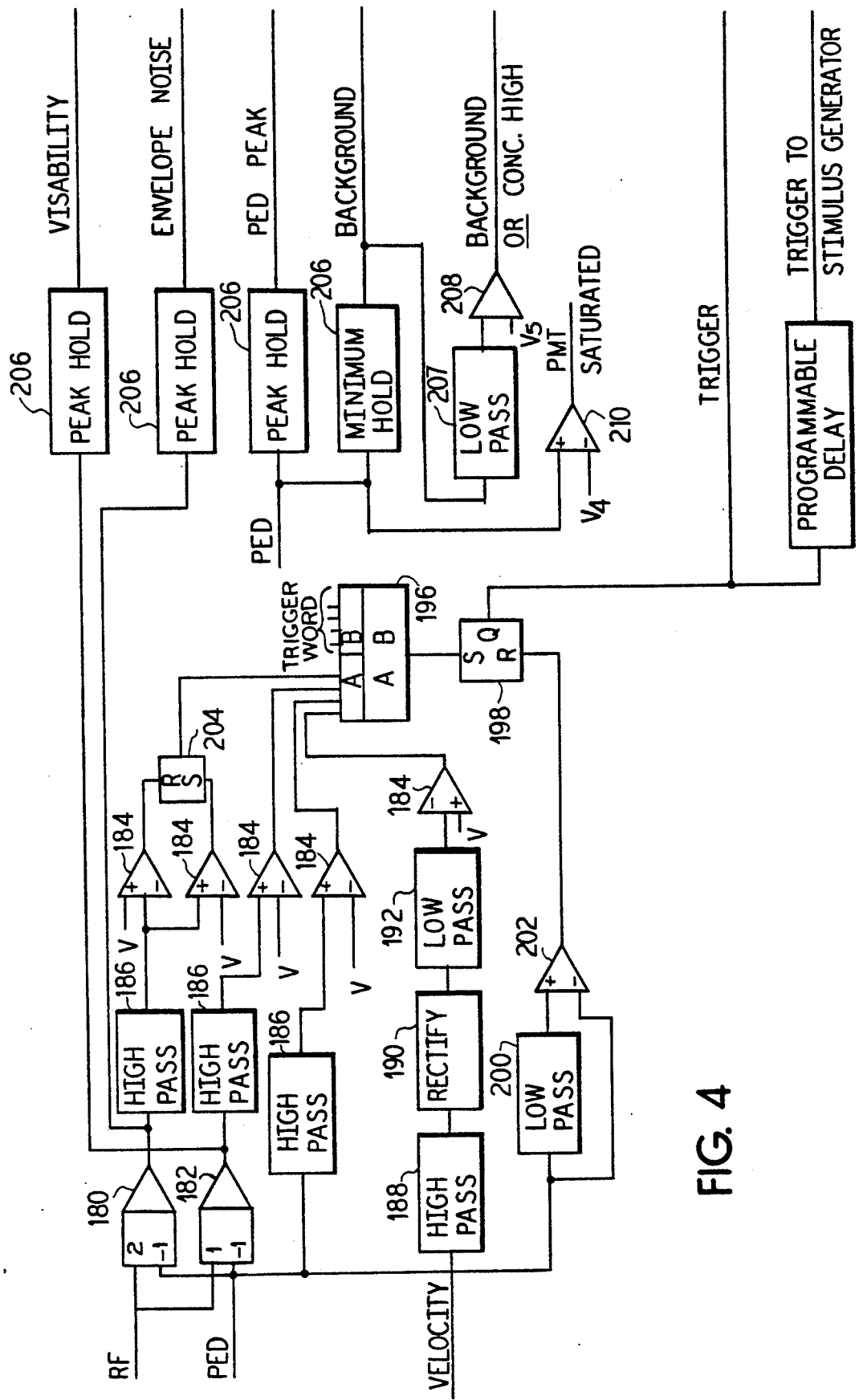
FIG. 4 is a block diagram of the trigger circuitry used to initiate real time control of the system.

In FIG. 4 is shown the body of circuitry which generates trigger signals in response to the passage of particles through the sensing volume. This circuit performs rapid analog calculations on the signals from the Doppler processor and generates signals which may be used to control the data acquisition system, the stimulus generators and so on. Analog summation blocks 180 and 182 perform the operations 2*RF−PED and RF−PED. These signals represent the detected envelope noise and visibility of the particle sensed by the Doppler processor. A bank of comparators 184 coupled to the appropriate elements via high pass filters 186 produce three digital outputs. Use of the high-pass filters allows the triggers to function correctly even when large adjustments are made in the PMT 44 gain or under adverse optical conditions. The comparators 184 may have a single trip point or two comparators may be used in conjunction with a latch 204 to produce a comparator with adjustable hysteresis.

The velocity signal is processed by passing the raw signal through high pass filter 188, a rectifier 190 and a low pass filter 192, all followed by a comparator. The high pass filter 188 is set to reject any signals due to stimulated motion of the particles and, thus, passes only the noise present in the discriminator output. The low pass filter 192 is chosen so that the cut-off is somewhat lower than the lowest frequency of excitation. The comparator 194 associated with this branch is directly coupled to the output of the low-pass filter 192. The output of this branch is a fourth digital signal which represents the noise content of the velocity signal. The comparator outputs are compared to a trigger word by logical comparator 196 to produce a start signal which sets the level of an R/S flip flop 198 which remains set until it is reset. Gating to allow "don't care" inputs may be added to allow more flexibility in setting up the comparator. In normal use, one branch of the trigger output may be delayed so that the particle motion is measured for an interval before the stimulus applied to the particle is changed. The reset signal is derived from a comparator 202 by comparing the pedestal signal to the average of the pedestal signal estimated by a low pass filter 200. This combination tracks the baseline of the pedestal signal and chatters when the pedestal is descending from a local maximum. As a result, the latch is reset at the end of a burst.

Optical Scattering

A useful outcome of the signal processing described above is that the optical scattering characteristics of particles may be determined simultaneously with the particle motion. The optical scattering signals are tracked using analog peak and minimum hold circuitry 206. The hold circuits 206 are reset after each burst. This allows the data rate associated with analysis of the scattering signals to be reduced to one datum per burst per parameter. In general, there is not enough information in the scattering signals to merit formal time series analysis.

A comparator 210 responds to the pedestal amplitude and has a threshold which is set to flag saturation or over-current in the PMT 44. This sets an error flag and removes the bias voltage from the PMT 44. The mean background optical scattering level is taken by Low Pass Filter 207 and sensed by a comparator 208. If the background level is high, the system is experiencing relatively high coincidence. A dilution cycle is initiated and an error flag in the data is forwarded to the host computer.

This method of gating can also screen data coming into the system and rapidly classify signals belonging to particles in general classes. Several logic comparators may be used to provide a very rapid classification of particle signals into general groups. Large particles, for example, could be counted or classified by sensing the combination of a high pedestal signal and a low visibility signal. Conversely, a high visibility, low pedestal signal is characteristic of small particles. By extension, a filter and rectifier may be added to the velocity processing branch to crudely measure mobility due to a specific force. Another enhancement would digitize only various peak signal levels and apply the resulting data to a comparison process. Counters attached to each comparator output would then be used to obtain information similar to that obtained from conventional particle counters. Such arrangements may be useful in certain aerosol monitoring situations.

Generation of Stimulus Signals

According to the present invention, zero mean, orthogonal time series signals are used to control the forces acting on the particles. Since the mean is zero, there is no net motion of the particle with respect to the sensing volume as a result of the forced motion. This feature minimizes the sampling bias which would otherwise favor less mobile particles. Since the functions are orthogonal and the particle response is linear, it is possible to analytically separate the response of the particle due to each force. A useful series of orthogonal functions is the harmonic series, for example, sinusoids with frequencies following the pattern 0, 1f, 2f, 3f, 4f, ... nf. These are orthogonal over the interval 1/f. A practical embodiment uses octave harmonics produced by binary division of a high frequency time base followed by subsequent analog filtering to remove unwanted harmonics. The derived sinusoids, thus, follow the series 1f, 2f, 4f, 8f ... nf. This embodiment is simple and economically constructed.

Two formats for the stimuli application are possible, open loop and closed loop. In the open loop approach, the forces are continuously applied to the sensing volume; while the closed loop approach first detects particles and applies forces only when a particle is present. An example of a closed loop approach is as follows: Initially no forces are present, and when a particle is detected in the sensing volume a stimulus, for instance a weak shock wave from a triggered spark gap or a pulse of intense light from a pulse laser, is applied to the sensing volume so that the stimulus acts along the LDV sense vector(s). Since the minimum required observation time is known (one period of the fundamental frequency), the two formats may be combined. In such combination, a stimulus is continuously present and, after a particle is detected, a second stimulus is applied and the response of the particle is observed. Alternately, the normally present stimulus is interrupted when the particle is detected and observation of the particle continues in the absence of stimulus. Sampling bias is also minimized when the closed loop format is used, since particles not being measured are not subject to applied force until after they are observed. A further extension of the closed loop method would allow the particles to be redirected or captured. The trigger feature of the stimulus generator block is intended to enable these modes of operation.

FIG. 8 is an exemplary embodiment of a stimulus generator for driving the transducers 90 and 92, for example. The time base signal is taken from a master oscillator 130, typically a 1 Mhz crystal stabilized device. The master oscillator signal is also fed to the real time processor at lead 140 as an acquisition clock signal. A divider chain 132 produces square waves which are harmonically related (for example, in octaves). Band pass filters 136 convert these square waves to high purity sine waves. Additive mixers 141 combine the outputs of the sine generators in any arbitrary combination to produce the stimulus signals which drive the power amplifiers 142, which in turn drive the transducers. A trigger signal from the real time processor may be used to activate the drive to any given transducer by action of an analog gate 138. Importantly, the output of the lowest frequency sine synthesizer 132 is output to the real time processor at a lead 144 to provide a synch signal. It is assumed that the generator components, power amplifiers and transducers all function as linear time invariant systems and that the phase relationship between various harmonics is stable.

Transducers and Field Monitoring

Figure 7:
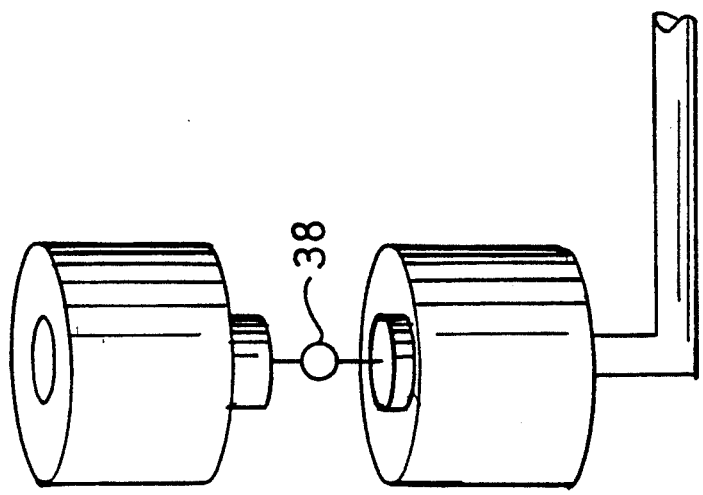
FIGS. 6 and 7 are schematic representations of various orientations of stimuli transducers for the apparatus.
Figure 6:
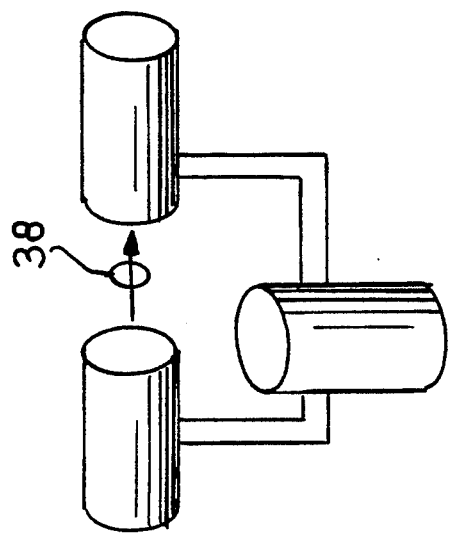

The following descriptions apply to transducers in general, acoustic, electric or magnetic. The transducers arrays are modular so they may be easily interchanged. This allows the arrays to be reconfigured for different particle testing schemes and allows the transducers to be easily replaced if they become damaged. As shown in FIGS. 6 and 7, the transducers 90 and 92 may be arranged along either a horizontal axis, as in FIG. 6, or along a vertical axis, as in FIG. 7, or in both configurations. In FIG. 6, the transducers 90 and 92 are mounted horizontally on an adjustable positioning device 114. In FIG. 7, the tubes for carrying the sample toward and away from the sensing volume 38 extend through the transducers 90 and 92. The transducers 90 and 92 are connected to leads 144 and 146 which receive drive signals from power amplifiers 142.

FIG. 5 shows a typical arrangement of transducers used in multiple force measurements. A pair of loudspeakers 90 and 92 may be located on either side of the sensing volume 38 and are driven by a suitable power amplifier whose input signal is taken from the stimulus generator 58. A microphone 96 may be used to monitor the acoustic field generated by the loudspeakers 90 and 92, the output of the microphone 96 being amplified by an amplifier 98. The acoustic transducers 90 and 92 determine the overall dimensions of the arrangement. Between the two loudspeakers 90 and 92 is mounted a small permanent magnet or a solenoid winding 100 and a pair of electrical terminals 100 and 102 (one of the terminals being the magnetic pole piece in the illustrated embodiment) to which is applied an alternating high voltage. The high voltage is typically the output of a high turns ratio transformer 104 driven by a suitable power amplifier 106. The solenoid winding 100 is driven by a magnetic field control signal through a second power amplifier 108. The electrical terminals constitute a modulated electrostatic deflection system. The solenoid 100 is a corresponding magnetic field generating device. The electrical field is monitored by either a divider network 110, as shown, or by a simple capacitively coupled sensor located near the high voltage terminals. The divider includes a buffer 112 which provides a low impedance, low voltage reference to the analysis system.

By changing the geometry and arrangement of the electrical transducers, a number of electrical properties in addition to charge may be measured. For example, under some circumstances, the dipole moment of non-spheres or the dielectric coefficient of individual particles may be sensed. All that is required is that the force in question causes a measurable response by the particle under test. There is also the possibility that unwanted effects can interfere with a given measurement. For instance, induction charging may occur if conditions in the electrical transducer promote the formation of ions in the carrier gas. This condition may be avoided by working at voltages below the corona threshold for the electrode configuration in use. It may also be possible to measure these charging effects by this technique.

Figure 11:
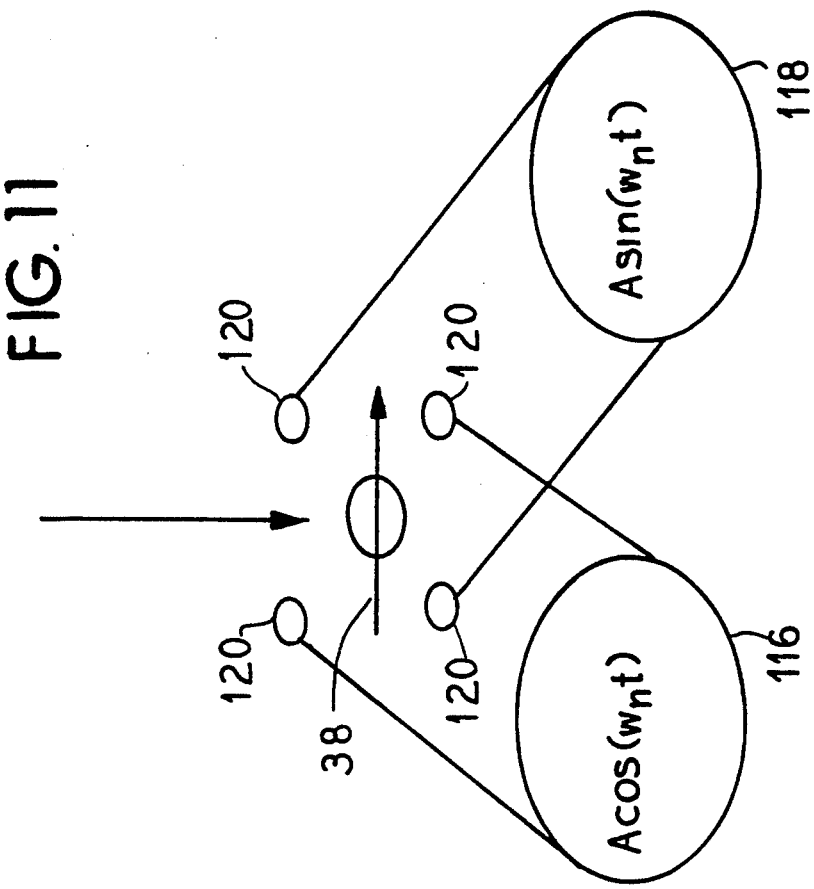
FIG. 11 is a schematic diagram of an electric quadripole arrangement for determining the shape of a particle.

FIG. 11 illustrates a transducer array which allows an extension of this technique. Electrodes 120 are driven by signals 116 and 118 which produce a rotating electrical field vector. Such an arrangement may allow detection of and discrimination of non-spherical particles when used alone or with the above described acoustic dipole. This is because the relative cross section (and hence drag) relative to the acoustic field may be modulated by the electrical field in the case of non-spheres.

The ideal sound-field for this technique is a highly localized plane wave; i.e., high velocity at the sensing volume and zero elsewhere. A realizable acoustical source which approximates these conditions is a virtual dipole source consisting of a symmetrically placed pair of transducers located on opposite sides of the sensing volume and driven in anti-phase. Performance of a dipole array is best when the transducers are identical in response and the separation of the transducers is small relative to the wavelength of the sound being generated. The acoustic transducers may be matched to the sensing volume by a pair of inverse conical horns 91 and 93. The horns produce a maximally flat wave front in the sensing region and result in a higher local acoustic velocity than is possible with direct radiators. Since the throat of the horns 91 and 93 is located near the sensing volume, mechanical clearance problems are minimized.

The nature of real acoustic transducers and the subtleties of acoustic propagation in the carrier gas are extremely complicated. For this reason, an indirect measure of acoustic field stability must be used. A signal at lead 154 is generated by a signal obtained from the microphone 96 located near the acoustic transducers. If a microphone 96 is used and the acoustic drive is monotonic, i.e. of a single frequency, then a simple stability monitor may be used. The microphone signal, buffered by an amplifier 156 is fed to a phase detector 158, wherein it is compared to the phase of the acoustic transducer drive signal, and then to a bounds detector 160. If the phase difference exceeds preset bounds, then an error signal is sent to the host computer over the a lead 154. An out-of-bounds condition indicates that a new calibration must be sought.

Alternatively, the microphone 96 output may be sampled by the host computer on a lead 162 so that a relationship between the error signal and the acoustic velocity at the sensing volume 38 may be determined empirically by testing with a precision aerosol while forcing the ambient temperature in the environmental chamber to vary. By comparison with prior art, this system does not derive a reference from the microphone, but tests the relation between the transducer drive signal and the microphone response. In this way, the stability, but not the absolute measure of the acoustic field near the sensing volume, may be assured. Absolute sensing of the acoustic field is done experimentally using test particles.

Since temperature is the most important parameter in determining acoustic propagation characteristics and other properties of a gas and since the apparatus may not always be in a constant temperature environment, a simple temperature transducer (for instance, a thermistor) located near the sensing volume may be used in lieu of a microphone to monitor gas conditions. In this case, a relationship between the measured temperature and the acoustic velocity at the sensing volume may be discovered in a way similar to the above-described microphone technique.

Other instruments which are sensitive to gas conditions that are not specifically related to acoustics may be used to determine the exact pressure and density of the gaseous media. These instruments should be readily interfaced to the host computer and serve to further minimize uncertainties in the operation of the instrument.

Figures 12A, 12B:
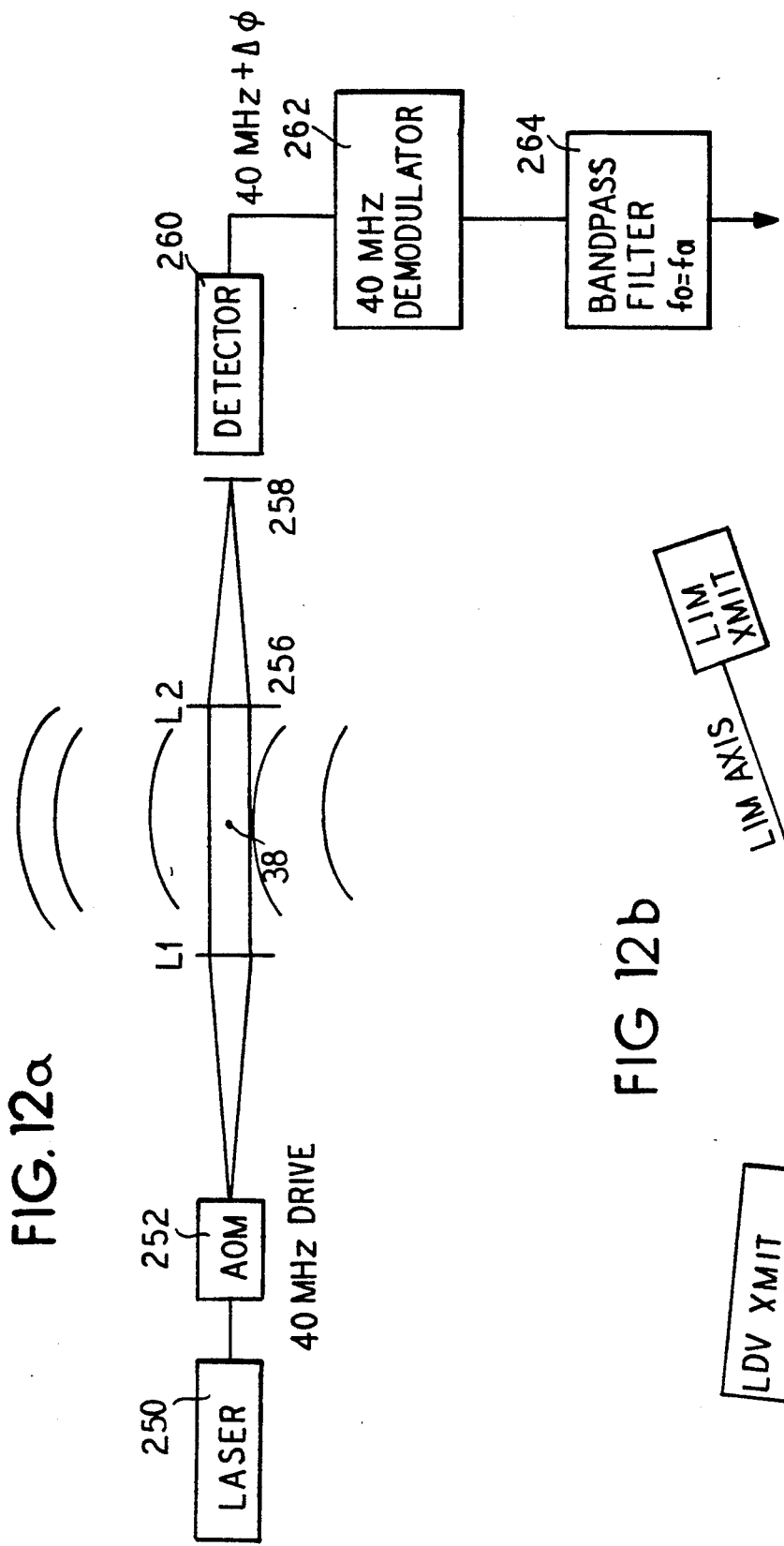
FIGS. 12a and 12b are diagrams of a laser interference microphone for use in sound field monitoring.

The acoustic motion component of the instrument may be used for remote sensing of ambient aerosols, that is, with the acoustic source and the LDV system mounted at a distance from the sensing volume and without the environmental enclosure, as in FIG. 18. In this case, knowledge of the local acoustic field is even harder to obtain. The presence of a microphone near the sensing volume may disrupt flow in the and, therefore, alter the local distribution of suspended matter. A differential laser interference microphone (DLIM) has been devised for this purpose. FIG. 12 shows an implementation of this device.

Generally similar devices are described in "Flow Diagnostics by Laser Interferometry" by G. Smeets; IEEE Transactions on Aerospace and Electronic Systems; Vol AES-13, No. 2. The action of this sensor is as follows: An output beam of a small HeNe laser 250 is split via a Bragg cell 252 to produce a beam shifted by the cell drive frequency and to produce an unshifted beam. A lens 254 is used to render the diverging beams parallel and focused in the regions close to but on opposite sides of the LDV sensing volume 38. A lens 256 refocuses these beams on a pinhole 258 whose size is sufficiently small to render the resulting fringes visible. The signal produced by the fringes sweeping across the pinhole is detected by an optical detector 260. Any phase modulation in the detected signal is recovered by a suitable demodulator 262 and further separated from any possible low frequency components by a bandpass filter 264. This apparatus takes advantage of the slight change in index of refraction with a change in pressure in a gas to perform the detection. Use of two laser beams allows the pressure difference and hence the local fluid velocity to be detected remotely. A frequency bias renders the probe immune to mechanical stability problems that otherwise effect long optical base interferometers. In practice, the interference microphone is operated off the plane of the main LDV transmitting system so that stray light does not reach the LDV receiving optics. It is contemplated that the waste beams from the LDV system may be used to operate the interference microphone, as well.

Particle Summary Data

Figure 16A:
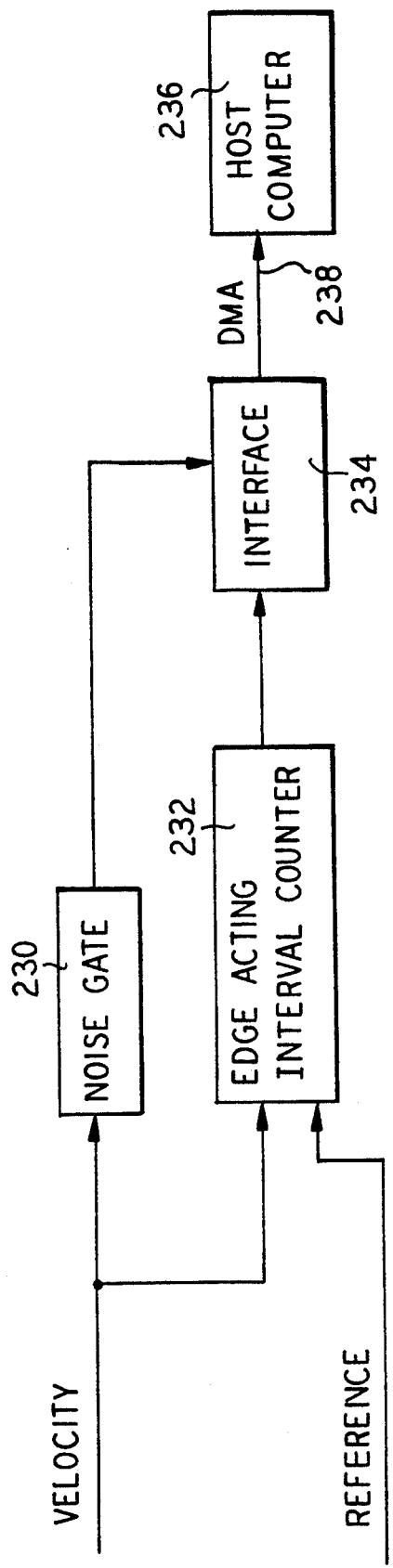
FIG. 16 is a block diagram of a phase only windowing system showing a representation of the intermediate data structure.
Figure 16B:
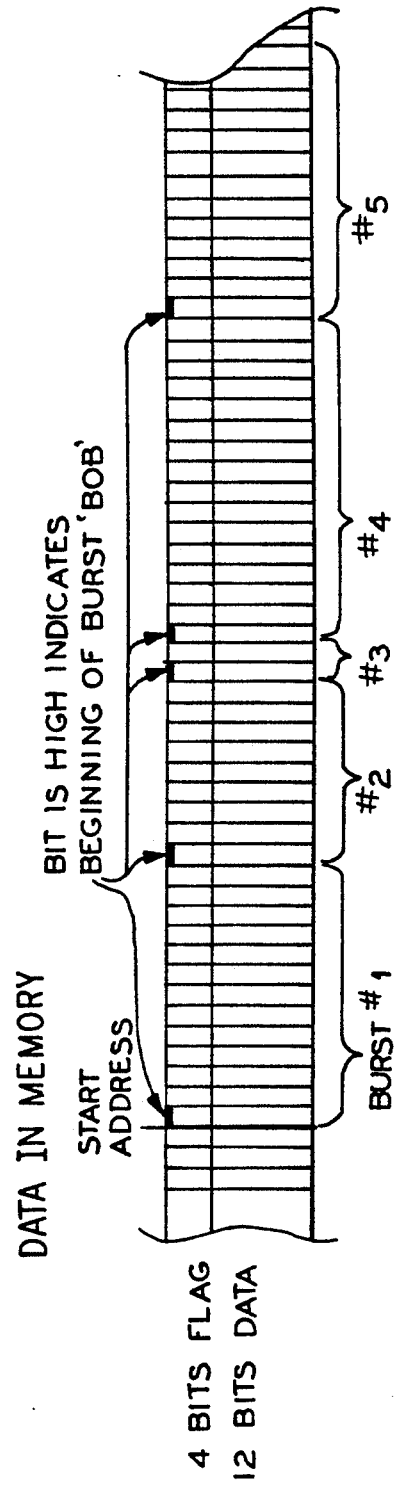

A simple instrument which extracts only one motion parameter and uses a self optimized windowing technique is provided. FIG. 16 is a block diagram of the phase-only windowing technique and of the data structure as assembled in the host computer. A noise gate block 230 is identical to that described in the above description of the trigger circuit. The edge-acting interval timer 232 measures the time between the rising edge of a reference square wave and the positive-going zero crossing on the recovered velocity waveform. Thus, the data rate is twice the reference frequency. In order to convert raw count to phase information, it is necessary to take the mean of an equal number of positive and negative going interval times. The interface 234 coupling this stream of data to the host computer 236 acts as a filter, forwarding data only when the noise gate senses a signal. Since the duration of any given signal is not known in advance, the interface also inserts a record mark or flag bit to indicate that a specific data is the beginning of a new burst. The interface communicates to the host over a direct memory access channel 238. This system allows the computer to determine the averaging window for a given burst. Because of the nature of the detection process, the signal quality in an LDV burst is always best at the middle of the burst and so a weighted mean can be constructed which dramatically improves the precision of the raw data taken by the system. The weighting must allow equal contribution from positive going and negative going edges and should be weighted to favor data from the middle of the burst. Another feature of this measurement technique is that particles whose response changes with time, such as evaporating liquid droplets, may be studied using a rolling mean acting on the contents of a given burst of measurements.

The processor used in an extended version is required to extract much more information from the signal and generate a summary record for each individual particle containing the following information: PARTICLE RECORD NUMBER, VELOCITY TERMS (which include mean velocity, phase and magnitude of various components, and measured noise power), OPTICAL SCATTERING TERMS (which include RF, Pedestal and Peak Visibility), TIME CODES (which include transit time and a time code), and AUXILIARY TERMS (which may include possible environmental or error flags). One of the tasks of the real time controller is to format the incoming data so that the net data rate requires only a direct memory access channel to a modest host computer, such as an EISA based personal computer (PC). This controller interposed timing flags into the record so that the phase of the reference signal is known to the host central processing unit (CPU) and performs sequencing and data formatting tasks. Other types of record marks are also introduced into the record at this point such as beginning-of-burst (BOB) markers and error flags. The trigger generator 300 produces three types of signals. These are peak levels (which are analog signals), threshold (which is a digital signal) and triggers (which are also digital signals). Since the host computer must know the phase of the excitation fundamental frequency, synch markers are also read into the record to indicate the position in time of the reference zero crossings. The most important analog signals (PED, RF and VELOCITY) as well as auxiliary analog signals must also be sampled. If an external digital signal processor (DSP) is not used, then by far the highest data rate required is that for the VELOCITY signal. This data stream is a highly over-sampled amplitude time series and only intermittently contains "good" data. Other data, such as the optical scattering signals and the burst duration, may be sampled only once per burst. By judicious use of flags, other system related data may be introduced at will into the data stream. The result of this preprocessing scheme is that the data record is much more compact than the data record would be for uniform sampling of all available signals at all times and that it contains only useful information which reduces host memory requirements and frees up valuable processor time. The interface controller communicates with the trigger block, the time-base, various timers and event counters and any other sources of data to be entered into the record. By way of illustration, FIG. 17 is a graphic representation of the formatted data record deposited in the host computer. The data acquisition system should also be versatile enough to allow conventional multi-channel sampling for use in diagnostic procedures and calibration.

Reduction of Velocity Data

Two types of digital signal processing may be applied to the reduction of velocity data. One is a pipe-lined method and works in real time with minimal delay using parallel processing. This method involves the addition of a processor array to the real time controller block or the addition of a vector processor to the host computer. The second method is for use when the data is analyzed by a conventional processor.

The pipeline process uses two branches, a gate branch (a) and a signal branch (b). The gate branch (a) defines a function ya3[n] which is a binary signal used to delimit a "BURST" of data:

$$ya1[n] = (x[n] - x[n - N1])^2;$$

$$ya2[n] = \frac{1}{N2} \sum_{m=n-N2+1}^{n} ya1[m];$$

$$ya3[n] = \begin{cases} 1 & ya2[n] \leq N3 \\ 0 & ya3[n] > N3 \end{cases}$$

$X(n)$ is uniformly sampled velocity data.

Because of the noise characteristics of the optical detection system, the envelope signals RF and PEDESTAL may also be used to define the window. Specifically the 2*RF−PEDESTAL signal closely follows the logarithm of signal ya2[n] and may be thresholded easily using a simple voltage comparator circuit to produce a gating signal equivalent to ya3[n].

The analytical branch of the processing chain extracts signal parameters using a running rectangular window of minimal length. These parameters represent the real $yb_{KI}$ and imaginary $yb_{KR}$ parts of the spectral components $\omega_k$ and the various other running means, such as noise power $yb_{NOISE}$ and the mean velocity $yb_{MEAN}$:

$$yb_{k1} = [n] = x[n]\text{COS}\left[\frac{n \omega_k T}{N4}\right];$$

$$yb_{k2} = [n] = x[n]\text{SIN}\left[\frac{n \omega_k T}{N4}\right]$$

$$yb_{kR} = [n] = \frac{1}{N4} \sum_{m=n-N4+1}^{n} yb_{k1}[m];$$

$$yb_{kI} = [n] = \frac{1}{N4} \sum_{m=n-N4+1}^{n} yb_{k2}[m];$$

$$yb_{MEAN}[n] = \frac{1}{N4} \sum_{m=n-N4+1}^{n} x[m];$$

$$yb_{NOISE}[n] = \frac{1}{N4} \sum_{m=n-N4+1}^{n} ya1[m]$$

In the pipeline process, the analytical results are averaged over bursts which are determined by the gating signal. If the variable ya3[n] is a weighted binary, that is, if its value is allowed to range from 0 to some positive value, then a weighted window results. This is computationally more intensive but will give better results with the proper weighting function. BURST is the number of times the gate signal has been 1 and returned to 0:

$$D_{BURST} = \frac{\Sigma ya3[n] \, ybk[n - N5]}{\Sigma ya3[n]} \quad \begin{array}{l} \text{while } ya3[n] > 0 \text{ until } ya3[n] = 0 \\ \text{if } ya3[n - 1] > 0 \text{ and } ya3[n] = 0 \\ \text{then; BURST} = \text{BURST} + 1 \end{array}$$

If the operations involving trigonometric functions are converted to sign-only operations, additional simplicity may be gained; however, care must be taken since the odd harmonics of a fundamental frequency also contribute to these sums.

The constants used in the above pipeline are: N1—Comb filter spacing; N2—comb filter smoothing; N3—Acceptance threshold; N4—Signal window and length of fundamental in samples per cycle; and N5—Delay between processing branches a and b.

The pipeline process described above is not applicable when the signal processing is conducted on that is data already available in the memory space of a single processor, such as when raw or formatted data in forwarded over a DMA channel. For this reason, another set of procedures have been devised. An especially useful technique works on data which has been pre-windowed, in other words, data is not forwarded to the host computer unless signal conditions are good. In this case it is easier to compute the boundaries of an appropriate window and to simply perform multiple analyses on the data in this window.

The first stage of such a process is to identify the center of the burst and then to find the largest n cycle window available within the data:

$$\text{START}' = \text{START} - N6;$$
$$\text{END}' = \text{END} - N7;$$
$$\text{MID} = \frac{(\text{START}' + \text{END}')}{2};$$

$$\text{HALFWIDTH} = (\text{START}' - \text{MID}) \bmod (N4 \; 2)$$
$$\text{START}'' = \text{MID} - \text{HALFWIDTH};$$
$$\text{END}'' = \text{MID} + \text{HALFWIDTH}$$

N6 is the start delay of the windowing circuitry and N7 is the stop delay. N4 again is the minimal window length based on the sampling frequency and the fundamental of the excitation.

Another method computes a window occupying a fixed percentage of the available signal. This procedure automatically adjusts to variable flow conditions.

After the window is established the following formulae may be used to extract the summary data:

$$D_{MEAN} = \frac{1}{\text{END}'' - \text{START}''} \sum_{n=\text{START}''}^{\text{END}''-1} x[n];$$

$$D_I = \frac{1}{\text{END}'' - \text{START}''} \sum_{n=\text{START}''}^{\text{END}''-1} x[n]\text{SIN}\left[\frac{n\omega_k T}{N4}\right]$$

$$D_R = \frac{1}{\text{END}'' - \text{START}''} \sum_{n=\text{START}''}^{\text{END}''-1} x[n]\text{COS}\left[\frac{n\omega_k T}{N4}\right];$$

$$D_{NOISE} = \frac{1}{\text{END}'' - \text{START}''} \sum_{n=\text{START}''}^{\text{END}''-1} (x[n] - x[n + N1])^2$$

The data computed in this manner are equivalent to the data computed by the pipeline process above and are treated as such in further processing.

The above processes yield the two complex components $I_n$ and $R_n$ of any spectral term in the velocity signal. The next stage in data reduction is to analyze the database resulting from accumulated particle records. The complex velocity pairs may be retained through subsequent processing or the pairs may be transformed to polar form at any time after the burst data is generated. It is more natural to think in terms of the polar expressions, i.e., magnitude and phase, so the data in the illustrations is shown in this form.

Figure 10A:
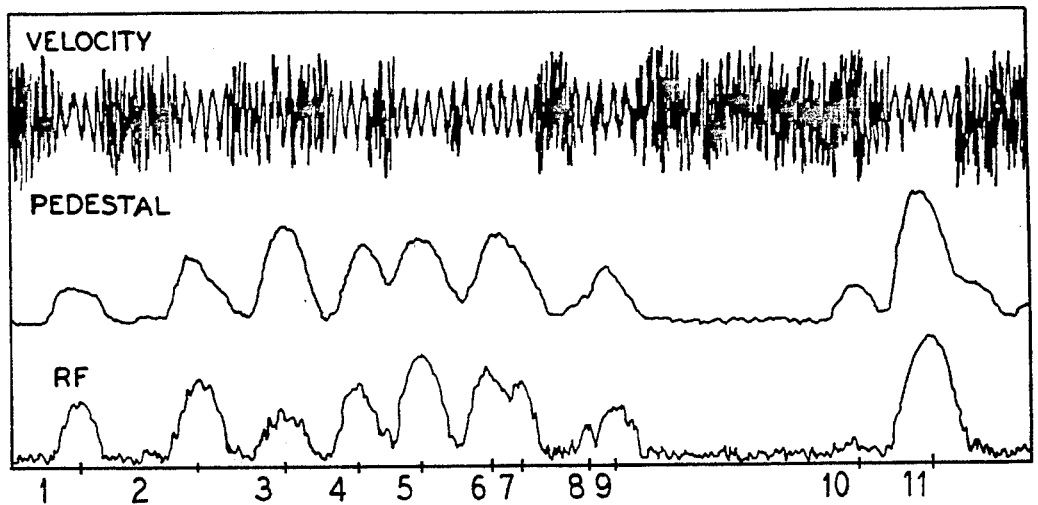
FIG. 10 is a graphical representation of raw and processed signals derived from the operation of the present invention.
Figure 10B:
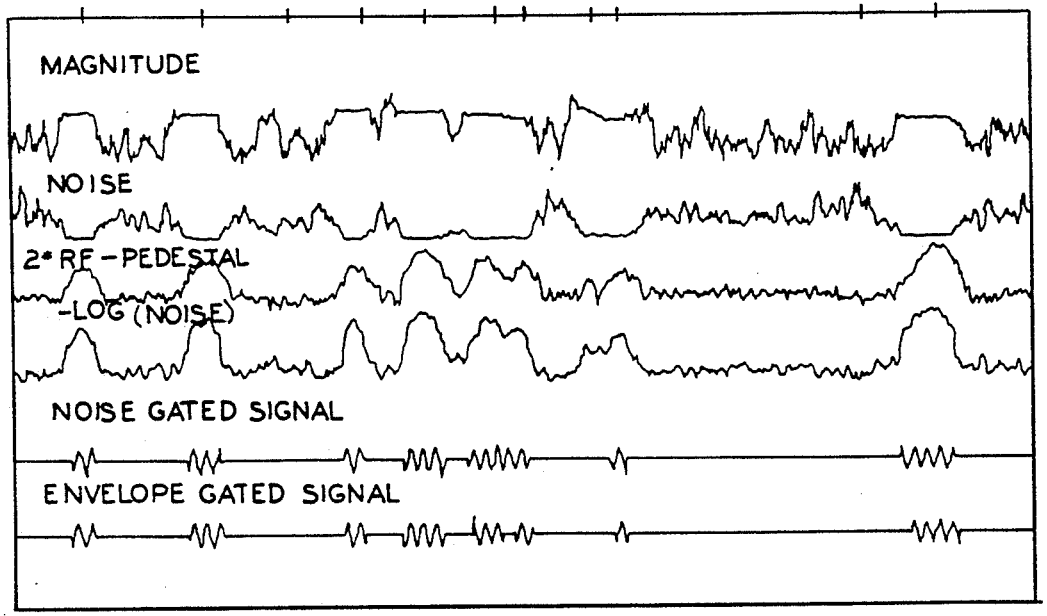

The graph in FIG. 10 illustrates steps in the first stage of signal processing, which is extracting of individual particle records from continuous time domain signals. In this illustration, the test particles were 0.5 μm spheres, the flow direction was perpendicular to the LDV sense vector, and the only excitation present was a 25 KHz acoustical field. This segment of signal has a duration of 3.25 ms and contains events related to 11 or so single particles, some of which overlap. The top three signals, VELOCITY, PED and RF are digitized directly from the outputs of the Doppler processor.

Formulas and more specific definitions for computed signals are given below. For ease of presentation, all signals have been normalized to their own extrema, and time delays inherent in the processing have been eliminated in each case by change of origin on the time axis. The scale of the horizontal axis may be ascertained by inspection since each period of the sinusoidal portion in the VELOCITY signal is exactly 40 μs. MAGNITUDE $= (ybk_I^2 + ybk_R^2)^{\frac{1}{2}}$ is the windowed average of the detected audio component in the velocity signal. PHASE is not shown but is computed by PHASE $= ARG\ (ybk_I / ybk_R)$. NOISE is the windowed average of the detected noise power in the velocity signal, wherein NOISE $= yb_{NOISE}.2*RF - PED$ is noise power computed using the above described shot noise formula. $-LOG(NOISE)$ is offered for comparison and is simply the logarithm of the computed NOISE signal. It is significant that the envelope of the $-LOG(NOISE)$ signal closely follows that of the $2*RF - PED$ signal since this supports the computation of signal quality based on the optical scattering measurements alone.

There are a number of subtle relationships between the signals. The signals NOISE GATED and ENVELOPE GATED are illustrations of the functional qualities of two possible gating signals. The envelope technique manifests minimum delay and, hence, is suitable for use in real time operations. The noise gating technique is more general and supplies additional information which may be used in subsequent processing.

The objective of this stage of signal analysis is to determine the light scattering properties and the motion of individual particles and to exclude signals due to coincidence or multiple scattering. To illustrate this, it is necessary only to inspect the record of FIG. 10. There are four types of events embedded in this record. Events 1, 2 and 11 are examples of isolated single particle bursts. In all three cases, the Pedestal signal starts at background level and returns to background level. These records are most certainly individual particle events. Events 3 and 10 are also single particle events, however, the signal-to-noise ratio SNR basis of shot noise assessment is unity or less. These two events thus represent grazers, in other words, particles which scattered light from a low visibility region of the sensing volume. There is no velocity information contained in these events, yet the events are distinct. Events 4 and 5 are single particle events which are separated by a scattering level well above background, yet the envelope gating method separates events 6 and 7 but the noise gate method does not, and neither gating method detects event 8.

Note that the PEDESTAL channel establishes less distinction (peak to dip ratio) than the RF signal and that both the $2*RF - PEDESTAL$ and the NOISE channel distinctly bracket this type of event. In the event that the gating established by either method passes a coincidence event of this type, it will be rejected by the post processing steps on the data base since the NOISE item in the summary line belonging to this "particle" will be noticeably above the mean for particles with otherwise similar responses. Since this method can clearly separate coincidence $\{(6,7,)(8, 9)\}$ and near coincidence $\{(4,5)\ (6,7)\}$ events, it is possible to treat the measured response in terms of single particle response. The nature of events 6, 7, 8 and 9 are much harder to ascertain. Are these signals the result of two particles or four? Unless there is something drastically wrong with the transmitting optics, such as contaminated lenses, these signals are the result of serial coincidence, in other words one particle is entering the sense volume just as another is leaving.

In FIG. 15, an example of summary data is superimposed on graphs of the associated raw signals. In part A, the entire burst is enclosed in the acquisition frame and the excitation is a 25 KHz sound field. In part B, an acoustic field at 6250 Hz acts in concert with an electrical field at 12500 KHz and a non-varying magnetic field. The data field is organized as follows: ID number, VELOCITY, OPTICAL, and TIME. This example omits other possible data types such as FLAGS or other due to the limitations of the data acquisition system used in this version.

Database Computations

The second stage of analysis is performed in batches on the accumulated database. The routines in use are familiar to data base practitioners and, thus, will not be mentioned further. This implies that size, charge, etc. are not normally computed until a number of particle records have been acquired. As a result, a number of internal checks on the consistency of the data are possible and the process is calibrated on the fly.

For unit density (1 g/cc) spheres in air, the maximum phase response of 75 degrees relative to the motion of the gas itself. This maximum occurs when the magnitude of the particle motion is approximately 10% of the magnitude of the gas motion. So if one attempts to measure the diameter of suspended particles by measuring the phase response alone as in the known methods, the interpretation is ambiguous for values of phase toward 75 degrees and strictly speaking at any phase. This problem is avoided if both the phase and the magnitude are taken simultaneously. There are several possibilities: Because phase response is more sensitive to the diameter at the small diameter end of the response function, a look up table based on phase is still useful, predicate on the relative amplitude of the response. A least squares polynomial may be substituted for the look up table. This requires less memory space and results in less quantitization error. This too should be predicate on amplitude. The amplitude response itself may be used to determine the size of the particles (see the Gucker reference cited in the introduction).

A far more elegant approach overcomes these limitations, however. Any given pair of <phase, amplitude> measurements corresponds to a unique pair of <diameter, density> attributes. The set of equations is soluble by numerical means. A variation of the secant method provides an iterative procedure which converges toward the desired result. In practice, limits are set on the convergence and the result is tested against the measured response until it is finally within specified bounds, at which point a solution is declared. The ultimate resolution depends upon the resolution of the detection process. In the preferred embodiment, data reduction is performed using polynomial or numerical solutions rather than look up tables. Because the measurements are uniquely obtained for each particle, distribution statistics may be calculated in a straight forward manner.

The database is normally extended in the number of columns as transformations are worked on the raw data. This maintains the integrity of the original data and allows future reinterpretation of the set, if necessary.

Another easily obtained parameter is the visibility V, which is equal to $I_{RF}/I_{Ped}$, so that:

$$Log(V)=LOG(I_{RF})-LOG(I_{Ped})$$

Visibility is a particle size related function and may be applied to the measurement of liquid droplets and the like (see the prior art cited hereinabove).

Some coincidence events inevitably come into the record aliased as single particles, these records are eliminated by statistical filtering using the noise and duration items in the summary data set. The noise power in a discontinuous signal such as results from coincidence is generally evidence to discard that item.

Self Calibration

The acoustic field monitors sense the stability of the acoustic velocity but do not actually measure the acoustic velocity of the gas at the sensing volume. A classical method of estimating the acoustic velocity in acoustic particle measurements is to use extremely small tracer particles and assume that the tracer particles follow the motion of the gas very closely. This is the approach taken by Gucker and Doyle (see above).

A second approach uses precision aerosols and to assumes that the response of these particles is known relative to the gas velocity. The usefulness of this technique depends upon which model is used to predict the response of the particles. If an inappropriate model is used, then there may be extremely large errors in the computed measurements, even if the particle velocities are determined very precisely. Stokes law, for instance, results in unacceptably large errors and leads to an aliasing phenomena when only the relative phase of the particle vibration is used to determine size. Since the particle phase response is double valued in the more accurately stated acoustic transfer function, a large particle and a small particle may share the same phase. Thus, it is not possible from phase alone to determine the size of a particle from its acoustic response. The present method evaluates both the components of the particle response in making a size determination.

Another possibility is to use the interaction of multiple forces to achieve calibration. For instance the combination of electrical and acoustic forces may be used to determine the acoustic velocity of the gas. This may be done if the phase of the electrical field is accurately known and functional mapping is used: $\phi_a(\phi_c)=P(\phi_e)$, where $P(\phi_e)$ is an approximating polynomial. The use of this type of calibration is a unique feature of the present invention. Since the electrical field phase may be directly measured, the acoustic field phase is then accurately determined any time that a charged particle is observed. There are fewer errors if signals from electrically mobile, small particles are used. Using this method, there is no need to perform any calibration to determine the acoustical phase.

A fourth method is based on the observation that the maximum acoustic phase is a function of the density of the particles. A hetero-disperse aerosol is introduced and the response of the particles is recorded. The first step is to estimate the maximum observed phase shift and the maximum observed particle velocity. If the density of the material in the hetero-disperse sample is known, and the maximum phase of the particle vibration is estimated, then the phase of the acoustic field may be estimated based on the theoretical response. The maximum observed velocity is a reasonable estimate of the acoustic velocity. To refine this further, the recorded signals with velocities less than 0.5 max are selected. The relative phase and amplitude are then adjusted until the computed mean density of the measured particles is equal to the bulk density of the material from which they are formed. When this method is used, the only assumption is that the acoustic field is stable, hence, it is desirable to use one of the previously describe field monitors.

Sampling and Flow System Control

In measurements involving powdered materials for various industrial processes, it is desirable to measure the distribution of particle diameters and the tribo-charging level acquired by the materials under conditions which simulate those found in the processes. The dispenser and sampling system shown in FIG. 1 is intended to emulate these conditions.

A hetero-dispersion of powder analyte is produced by impinging a brief pulse of air (or other gas) on a small sample of powder. Alternatively the dispenser may be mechanically driven by a brief vibratory impulse provided by an electro-mechanical vibrator. The powder dispensing mechanism is a small "cup" or carrier formed from perforated metal or wire mesh. It is important to insure that the dispenser has a relatively large area of exposed metal which the powder can contact when it is expelled. This insures that representative tribo-charging levels occur in the dispersion process. The dispensing cup and related hardware is located at the top of a tubular column which serves simultaneously as a vertical elutriator and subsequently as a holding chamber for the dispersed material. The bulk charge delivered to the material can easily be sensed by measuring the residual charge on the dispensing cup after the sample is dispersed.

The dispenser column or other sample preparation means is typically located above the environmental housing enclosing the applied force transducers and the LDV sensing volume. The sample is moved in a gas stream from the sample preparation chamber toward the sensing volume under a controlled flow.

Due to gravitational settling, the first particles to reach the sensing volume after the dispenser is actuated are large particles with relatively high settling velocities. The settling velocities may be accounted for by knowledge of the time of dispersion and the time of arrival, but it is far better to use an LDV sensor set up to measure the vertical component of the particle velocity. In a given sample, these are least numerous but may contain the largest mass concentration in the sample. Accounting for such particles may, thus, be of prime importance.

The measurement process will occasionally experience overloads due to excessively high concentrations of analyte. Symptomatically, the optical background will be continuously high and several types of coincidence events will occur frequently. When this condition is detected, a dilution cycle is initiated. This proceeds by introducing a known flow to the upper chamber for a fixed period of time. It is assumed that introduction of a volume of gas equal to the volume of the holding chamber will cause a dilution of 50%, just as subsequent equi-volume dilution will give 25% dilution, and so on. After each stage, the dilution process is interrupted and the signal conditions are again assessed, and if the sampling conditions are judged "good" then the dilution is stopped. The reason for this procedure is to insure relative stability in the counting efficiency of the system. When conditions of high background noise and high coincidence are present, relative counting efficiency will be different from the efficiency determined for isolated bursts against low background noise (i.e., ideal operating conditions). The real time controller/trigger block provides signals to control the sample dispersion device, which are the dilution valves in the preferred embodiment. Since the sampling system operates at very low flow rates, a very low but stable pressure difference must be maintained between the sample holding chamber and the housing which contains the sensing volume. During a dilution cycle, this condition is violated and results in high flow rates during the cycle. For this reason, the controller communicates the occurrence of dilution events to the main data acquisition/logging system.

The real time control block may also be set to perform the following functions: 1) Cleansing the measurement chamber. If the count rate falls below a preset level, indicating that no further sample is present, the system is flushed with clean gas and subsequently the powder dispenser is reactivated. 2) Communicating the need for service to the equipment. If the background photo-current is high, the dilution valve to the holding chamber is activated for a fixed time. The dilution is repeated until background count rate is acceptable, at which time the dilution is halted. A run may also be terminated by the host computer. If the statistics of the measured distribution stabilize, or after a fixed time, the run may be halted and the chamber flushed.

Although other modifications and changes may be suggested by those skilled in the art, it is the intention of the inventor to embody within the patent warranted hereon all changes and modifications as reasonably and properly come within the scope of his contribution to the art.

I claim:

1. A method for analyzing particles in a laser doppler velocimeter, comprising the steps of:
   supplying particles to be tested to a sensing volume of the laser doppler velocimeter;
   exciting the particles in the sensing volume with a plurality of forces which are orthogonal over an interval corresponding to a cycle of a fundamental frequency of said forces and which have a zero mean force over said interval; and
   sensing resulting motion of the particles in the sensing volume to obtain a sensor signal, wherein said sensor signal includes components representative of physical characteristics of the particles.

2. A method as claimed in claim 1, further comprising the steps of:
   dividing said sensor signal into two channels, a first of said two channels being a radio frequency component and a second of said two channels being a low frequency component;
   applying logarithmic analysis to said first of said two channels to produce a logarithm of the radio frequency component;
   discriminating said radio frequency component to produce a signal proportional to particle velocity; and
   applying logarithmic analysis to said second of said two channels to obtain a pedestal signal.

3. A method as claimed in claim 2, wherein said step of applying logarithmic analysis to the sensor signal occurs in real time.

4. A method as claimed in claim 1, further comprising the step of:
   verifying said sensor signal as a signal from a particle encounter with a single particle in the sensing volume, including:
      statistically filtering sensor signals to detect harmonic distortion and discontinuities in a velocity signal, and
      rejecting sensor signals from particle encounters having at least one of harmonic distortion and discontinuities in the velocity signal.

5. A method as claimed in claim 1, further comprising the steps of:
   recording a complete history of a particle encounter; and
   conducting a summary analysis on said recorded complete history, said summary analysis being at least one analysis from the group consisting of: mean velocity, phase and magnitude of a sinusoidal component, noise content of a velocity signal, logarithms of peak RF and pedestal scattering signals, time of arrival and duration of measurement.

6. A method as claimed in claim 1, further comprising the step of:
   summarizing particle encounter data, including: applying a weighted mean to particle encounter data, flagging data for inclusion in a data summary.

7. A method as claimed in claim 1, further comprising the step of:
   estimating noise power (SNR) in the sensor signal from a radio frequency component (RF) and from a pedestal envelope component according to the formula $Log(SNR) = 2*Log(RF) - Log(Pedestal) + a\ constant$.

8. A method as claimed in claim 7, wherein said step of estimating comprises the steps of:
   filtering the sensor signal to remove components of harmonic motion,
   detecting the filtered signal with a square law detector;
   smoothing the detected signal;
   comparing the smoothed signal to a threshold level.

9. A method as claimed in claim 1, wherein said step of analysis includes:

applying a moving window analysis to a time series velocity signal of said sensor signal, including:
statistically weighting a measurement so that larger contributions are made by portions of the velocity signal which contains at least a quantity of measured noise,
flagging a beginning of a new particle burst,
windowing for analysis particle encounter data after the beginning of the burst but before an end of the burst, and
sensing an end of the burst.

10. A method as claimed in claim 1, further comprising the steps of:
bracketing said sensor signal; and
analytically separating out from said bracketed signal effects of each of said plurality of forces.

11. A method as claimed in claim 1, further comprising the steps of:
applying coincidence excluding measures to said sensor signal, including:
determining whether a level of a pedestal signal of said sensor signal rises above and returns to a background scattering level,
determining that a sinusoidal portion of a velocity signal of said sensor signal is continuous in an analysis window, and
post processing to eliminate signals from said sensor signal with markedly poor measured signal to noise ratio.

12. A method as claimed in claim 1, wherein said plurality of forces having orthogonality include simultaneous electrical, acoustic and magnetic forces.

13. A method as claimed in claim 1, wherein said laser doppler velocimeter is a multi-axis velocimeter and said plurality of forces are orthogonal over one of an interval corresponding to a cycle of a fundamental frequency of the forces and are applied along mutually perpendicular vectors.

14. A method as claimed in claim 7, wherein said step of estimating noise power is performed on a particle velocity component of said sensor signal.

15. A method as claimed in claim 14, further comprising the step of:
weighting a measurement of velocity inversely to a noise content to validate said sensor signals.

16. An aerosol particle analyzer, comprising:
a laser optical means for generating a pair of crossed laser beams forming a sensing volume of interference fringes; and
particle preparation means for directing a sample of particles to be tested into said sensing volume;
transducer means for generating a field in said sensing volume to cause forces on particles within said sensing volume;
optical detection means for converting scattered light from particles in said sensing volume into a first electrical signal;
processing means for extracting from said first electrical signal other extracted electrical signals indicative of particle velocity, and signals proportional to logarithms of RF (radio frequency) and pedestal components of the scattered light; and
means for establishing validity of the velocity signal based on a relationship between a signal to noise ratio of the velocity signal and a linear combination of two logarithmic signals: $Log(SNR)=2\cdot Log(RF)-Log(Pedestal)+$ a constant.

17. An aerosol particle analyzer as claimed in claim 16, further comprising:
monitoring means for monitoring said field, said monitoring means being external of said transducer means to monitor stability of said field.

18. An aerosol particle analyzer as claimed in claim 17, wherein said transducer means comprises a pair of controlled acoustic loudspeakers mounted on either side of said sensing volume, and means for driving said pair of controlled acoustic loudspeakers in anti-phase and wherein said monitoring means comprises a microphone mounted to sense an acoustic field in said sensing volume.

19. An aerosol particle analyzer as claimed in claim 16, further comprising:
self calibration means for transmitting a calibration signal to said optical detection means.

20. An aerosol particle analyzer as claimed in claim 18, wherein said microphone includes a laser interference microphone which uses waste beams of the laser optical means.

21. An automated single particle analyzer, comprising:
a controlled sample delivery system for delivering particle samples,
a laser Doppler velocimeter receiving the particle samples from said controlled sample delivery system,
particle motion forcing means for directing forces onto the particle samples in said laser Doppler velocimeter, said particle motion forcing means including a collinear array containing electrical, magnetic and acoustical transducers,
control means for controlling operation of said particle motion forcing means,
signal analysis means for simultaneously extracting particle motion parameters and optical scattering parameters of the particle samples in said laser Doppler velocimeter, and
means for self calibration of said particle analyzer.

22. An automated single particle analyzer as claimed in claim 21, wherein said particle motion forcing means includes a pair of inverse conical horn devices coupled to two transducers driven in antiphase to generate a controlled local high acoustic velocity soundfield.

23. An automated single particle analyzer as claimed in claim 21, wherein said particle motion forcing means is normal to an aerosol flow channel of said delivery system.

24. An automated single particle analyzer as claimed in claim 21, wherein said signal analysis means includes an optical sensor, and further comprising:
means for determining the gain and condition of the primary optical sensor using optical test signals.

25. An automated single particle analyzer as claimed in claim 21, further comprising:
means for recording summary data about motion and light scattering properties of individual particles in such a way that said summary data may be later retrieved and reinterpreted based upon overall content of an accumulated database.

26. An automated single particle analyzer as claimed in claim 21, further comprising:
means for sensing an overload of said sample delivery system; and
means for initiating a dilution cycle when an overload is sensed.

27. An automated single particle analyzer as claimed in claim 21, further comprising:
means for pulsing said sample delivery system to deliver a pulse of particle laden gas.

28. A method of calibrating a particle measuring apparatus, comprising the steps of:
a) acquiring a measured acoustic response of randomly sized droplets of known density, including
introducing the randomly sized droplets of known density into a sensing volume of the particle measuring apparatus,
applying forces of an amplitude and a phase to the randomly sized droplets,
sensing response motions of the randomly sized droplets resulting from application of the forces,
collecting the response motions;
b) analyzing the response motions collected in said collecting step to obtain an extrema measured acoustic velocity of the response motions and an extrema measured phase of the response motions to serve as an initial estimate of local acoustic velocity of the randomly sized droplets, and
c) adjusting said amplitude and said phase of said forces until larger particles in the response motions being collected in said collecting step lie substantially on a curve of the known density.

29. An aerosol particle analyzer, comprising:
a frequency biased laser Doppler velocimeter having a sensing volume;
particle preparation means for dispersing small samples of particles to be tested into a vertical holding chamber and thence into the sensing volume of said laser Doppler velocimeter;
a transducer means for generating acoustical, electrical and magnetic fields in said sensing volume to cause oscillating motions of particles within said sensing volume;
signal generation means for generating transducer control signals which are mutually orthogonal in time on an interval less than a transit time of the particles through the sensing volume;
optical detection means for converting scattered light from the particles in said sensing volume into a first electrical signal;
processing means for extracting from said first electrical signal other electrical signals which represent the logarithms of an RF component, a pedestal low frequency component and an analog of a Doppler frequency of the RF component;
means for analysis of combined logarithmic signals to provide a substantially instantaneous estimate of signal to noise ratio of a Doppler component;
means for windowed analysis of the Doppler component to extract components of particle motion due to said orthogonal control signals with the windowing being predicated upon an estimate of short term SNR of the Doppler component;
means for compiling data resulting from a single particle encounter to a database;
means for analysis of said database to yield information on optical, physical and dimensional properties of individual particles; and
means for compiling computed properties to yield estimates of distribution of properties in the sample.

* * * * *